United States Patent
Kuo et al.

(10) Patent No.: US 8,562,337 B2
(45) Date of Patent: Oct. 22, 2013

(54) ACTIVE ATTACHMENTS FOR INTERACTING WITH A POLYMERIC SHELL DENTAL APPLIANCE

(75) Inventors: Eric Kuo, Foster City, CA (US); Fuming Wu, Pleasanton, CA (US)

(73) Assignee: Align Technology, Inc., San Jose, CA (US)

( * ) Notice: Subject to any disclaimer, the term of this patent is extended or adjusted under 35 U.S.C. 154(b) by 1583 days.

(21) Appl. No.: 11/725,790

(22) Filed: Mar. 19, 2007

(65) Prior Publication Data

US 2008/0233529 A1    Sep. 25, 2008

(51) Int. Cl.
*A61C 3/00*    (2006.01)
(52) U.S. Cl.
USPC ............................................. 433/6
(58) Field of Classification Search
USPC ....................... 433/6, 7, 18, 21, 24
See application file for complete search history.

(56) References Cited

U.S. PATENT DOCUMENTS

| | | | |
|---|---|---|---|
| 4,793,803 A * | 12/1988 | Martz | 433/6 |
| 5,246,366 A | 9/1993 | Tracey | |
| 5,322,435 A | 6/1994 | Pletcher | |
| 5,356,289 A | 10/1994 | Watanabe | |
| 5,984,675 A | 11/1999 | White | |
| 6,309,215 B1 | 10/2001 | Phan et al. | |
| 6,572,372 B1 | 6/2003 | Phan et al. | |
| 6,604,943 B2 | 8/2003 | White | |
| 6,607,383 B2 | 8/2003 | Abels et al. | |
| 6,705,863 B2 | 3/2004 | Phan et al. | |
| 2003/0190575 A1 * | 10/2003 | Hilliard | 433/6 |
| 2006/0154195 A1 | 7/2006 | Mather | |
| 2006/0199141 A1 * | 9/2006 | Wen | 433/24 |

OTHER PUBLICATIONS

ISA/US, International Search Report and Written Opinion for International Application No. PCT/US2008/054595, 8 pages, Feb. 21, 2008.

* cited by examiner

*Primary Examiner* — Robyn Doan
*Assistant Examiner* — Matthew Nelson

(57) ABSTRACT

An active dental attachment. Specifically, an attachment device for interacting with a polymeric shell dental appliance is described. The attachment device includes an anchoring attachment body. A bonding surface is coupled to the anchoring attachment body, wherein the bonding surface is configured for anchoring the anchoring attachment body to a dental feature of a patient's dentition. A force-applying active mechanism is coupled to the anchoring attachment body. A polymeric shell dental appliance contact region is coupled to the force-applying active mechanism. The polymeric shell dental appliance contact region is configured to contact the force-applying active mechanism and apply a force generated by the force-applying active mechanism between the dental feature and the polymeric shell dental appliance when the polymeric shell dental appliance engages the force-applying active mechanism.

30 Claims, 18 Drawing Sheets

ACTIVE ATTACHMENTS FOR INTERACTING WITH A POLYMERIC SHELL DENTAL APPLIANCE

CROSS REFERENCE TO RELATED APPLICATIONS

The planning and fabrication of dental aligners, such as an exemplary elastic polymeric positioning appliance, is described in detail in U.S. Pat. No. 5,975,893, and in published PCT application WO 98/58596 which designates the United States, both entitled "METHOD AND SYSTEM FOR INCREMENTALLY MOVING TEETH," both of which are assigned to the assignee of the present application.

BACKGROUND

1. Field

Embodiments of the present invention relate in general to orthodontics. More particularly, embodiments of the present invention relate generally to active attachment devices that interact with a polymeric shell dental appliance to provide additional forces on a patient's dentition.

2. Related Art

Orthodontic treatments involve repositioning misaligned teeth and improving bite configurations for improved cosmetic appearance and dental function. Repositioning is typically accomplished by applying gentle controlled forces to a patient's teeth over an extended period of time. Due to the limited space within the oral cavity and extensive movements that some teeth must undergo, the teeth will often be moved throughout a series of intermediate patterns to properly arrange the teeth. For example, molars may be temporarily moved backwards (distalized) to create adequate space for movement of the incisors. Thus, a single patient treated with plastic aligners may experience an average of 25-30 aligner stages before achieving the final desired teeth arrangement.

Conventionally, repositioning of teeth has been accomplished by what are commonly referred to as "braces." Braces comprise a variety of appliances such as brackets, bands, archwires, ligatures, and O-rings. After they are bonded to the teeth, periodic meetings with the treating dentist are required to adjust the braces. This involves installing different archwires having different force-inducing properties, and/or replacing or tightening existing ligatures. Between the periodic meetings with the doctor, the patient may be required to wear supplementary appliances, such as elastic bands or headgear, to supply additional or extraoral forces. Although conventional braces are effective, their use is often a tedious and time consuming process and requires many visits to the doctor's office. Moreover, from the patient's perspective, the use of braces is unsightly, uncomfortable, presents a risk of plaque retention, and makes brushing, flossing, and other dental hygiene procedures difficult. Additionally, as conventional braces are fixedly bonded to the patient's teeth, the braces cannot be removed when the patient is eating.

An alternative to braces includes the use of elastic positioning appliances for realigning teeth. Such an appliance may be comprised of a thin shell of elastic material that generally conforms to a patient's teeth but each appliance is slightly out of alignment with the initial tooth configuration. Placement of the elastic positioning appliances over the teeth applies controlled forces in specific locations to gradually move the teeth into a new configuration. Repetition of this process with successive appliances comprising new configurations eventually moves the teeth through a series of intermediate arrangements to a final desired arrangement.

With traditional wire and bracket technology, the wire is tied to the bracket, such that the energy stored in the wire during the process of engaging the wire to the bracket gets released and converted into orthodontic tooth movement as the wire conforms back to this original undistorted shape. Shape memory alloys, for example, enable distortions that are stored in the wire to be gradually released over long periods of time.

Treatment using removable elastic positioning appliances occurs over increments of time. This occurs since the plasticity of the elastic positioning appliance is typically limited to a period of less than one week. That is, the elasticity of the elastic positioning device deteriorates quickly over a short period of time. As such, forces stored within the elastic positioning appliance typically can only be effectively applied over a period of approximately two weeks. As a result, a significant number of elastic positioning devices worn in stages are used over a long period of time to effectively provide orthodontic tooth movement.

Additionally, in some cases, orthodontic treatment may involve complex tooth movements or treatment plans requiring additional devices or accessories. That is, the forces applied by the removable elastic positioning appliances may not alone be sufficient to achieve these complex tooth movements or treatment plans. For example, the elastic positioning appliance alone may not be able to apply forces to surfaces of the teeth due to the location or characteristics of the surface itself of the tooth or of the surrounding teeth.

SUMMARY

Accordingly, various embodiments of the present invention disclose apparatus and methods for an active attachment device interacting with a polymeric shell dental appliance. Specifically, in one embodiment an active attachment device for interacting with a polymeric shell dental appliance is described. The active attachment device includes an anchoring attachment body. A bonding surface is coupled to the anchoring attachment body, wherein the bonding surface is configured for anchoring the anchoring attachment body to a dental feature of a patient's dentition. A force-applying active mechanism is coupled to the anchoring attachment body. A polymeric shell dental appliance contact region is coupled to the force-applying active mechanism. The polymeric shell dental appliance contact region is configured to contact the force-applying active mechanism and apply a force generated by the force-applying active mechanism between the dental feature and the polymeric shell dental appliance when the polymeric shell dental appliance engages the force-applying active mechanism.

DESCRIPTION OF THE EMBODIMENTS OF THE INVENTION

Figure 1:
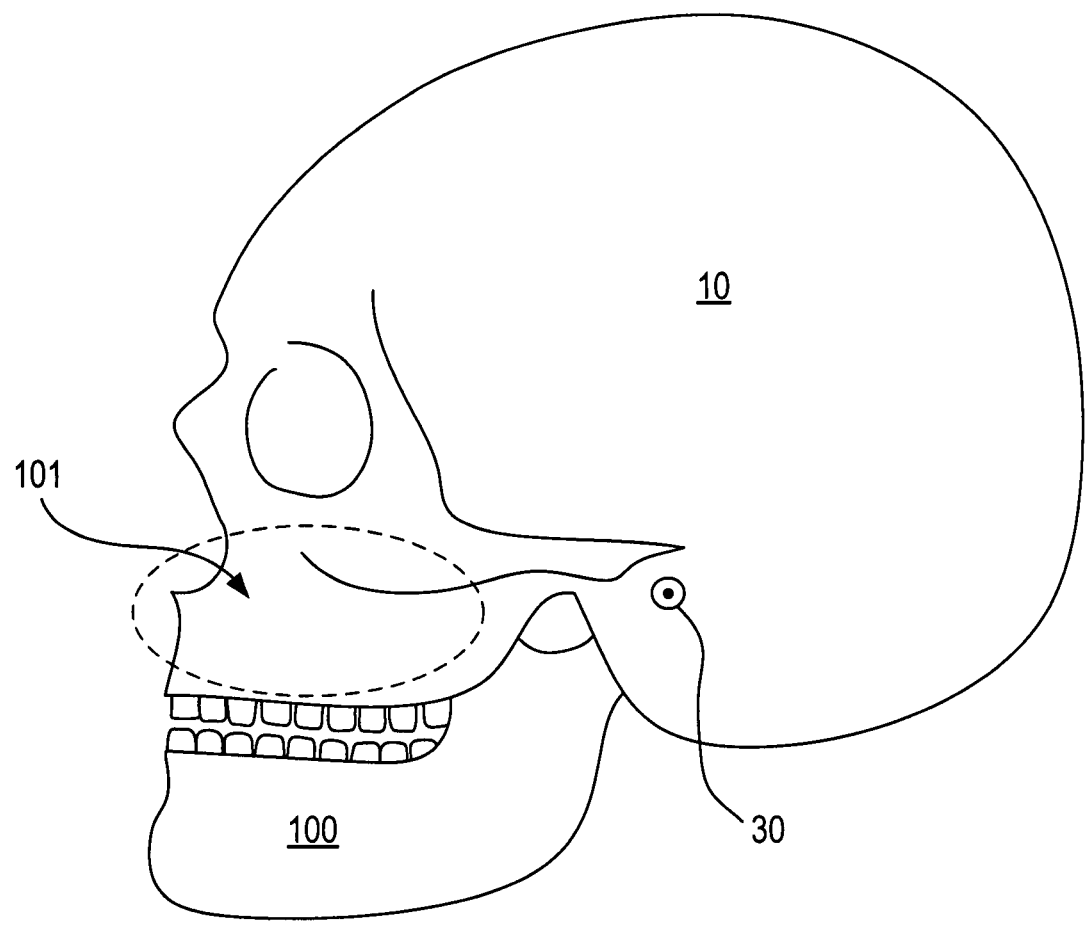
FIG. 1 is an elevational diagram showing the anatomical relationship of the jaws of a patient upon which teeth may be moved by the method and apparatus of embodiments of the present invention.

Reference will now be made in detail to the preferred embodiments of the present invention, apparatus and methods active attachment devices interacting with polymeric shell dental appliances for orthodontic treatment, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims.

Furthermore, in the following detailed description of the present invention, numerous specific details are set forth in order to provide a thorough understanding of the present invention. However, it will be recognized by one of ordinary skill in the art that the present invention may be practiced without these specific details. In other instances, well known methods, procedures, and components have not been described in detail as not to unnecessarily obscure aspects of the present invention.

Accordingly, various embodiments of the present invention disclose active attachment devices capable of interacting with polymeric shell dental appliances to apply forces used for orthodontic treatment. As a result, embodiments of the present invention provide for the above accomplishment, and further provide for the application of controlled forces over a large period of time when used with polymeric shell dental appliances. Still other embodiments of the present invention provide the above accomplishments, and further provide for a reduced number of polymeric shell dental appliances used in a course of orthodontic treatment. Other embodiments of the present invention provide the above accomplishments and further provide for complex movement of teeth previously unattainable through the sole use of polymeric shell dental appliances, which provides for more effective overall orthodontic treatment.

System and Method for Positioning Teeth

Orthodontic treatments involve repositioning misaligned teeth and improving bite configurations for improved cosmetic appearance and dental function. Repositioning is typically accomplished by applying gentle controlled forces to a patient's teeth over an extended period of time. Due to the limited space within the oral cavity and extensive movements that some teeth must undergo, the teeth will often be moved throughout a series of intermediate patterns to properly arrange the teeth. For example, molars may be temporarily moved backwards (distalized) to create adequate space for movement of the incisors. Thus, a single patient may experience an average of 25-30 aligner stages before achieving the final desired teeth arrangement.

Conventionally, repositioning of teeth has been accomplished by what are commonly referred to as "braces." Braces comprise a variety of appliances such as brackets, bands, archwires, ligatures, and O-rings. After they are bonded to the teeth, periodic meetings with the treating dentist are required to adjust the braces. This involves installing different archwires having different force-inducing properties or by replacing and/or tightening existing ligatures. Between meetings, the patient may be required to wear supplementary appliances, such as elastic bands or headgear, to supply additional or extraoral forces. Although conventional braces are effective, their use is often a tedious and time consuming process and requires many visits to the doctor's office. Moreover, from the patient's perspective, the use of braces is unsightly, uncomfortable, presents a risk of plaque retention, and makes brushing, flossing, and other dental hygiene procedures difficult.

In embodiments of the present invention, repositioning of teeth may be accomplished with the use of a series of removable elastic positioning appliances, referred to as "aligners". Such appliances comprise a thin shell of elastic polymeric material that generally conforms to a patient's teeth but each appliance is slightly out of alignment with an initial or immediately prior tooth configuration. Placement of the elastic aligner over the teeth applies controlled forces in specific locations to gradually move the teeth into the new configuration. Repetition of this process with successive aligners comprising new configurations eventually moves the teeth through a series of intermediate arrangements to a final desired arrangement. Conveniently and advantageously, the appliances are not affixed and the patient may place and replace the appliances at any time during the alignment process.

FIG. 1 is an illustration of a skull 10, upon which the repositioning of teeth is accomplished with a series of removable aligners, in accordance with one embodiment of the present invention. The skull 10 includes a maxilla or upper jaw 101 outlined approximately by the dotted circle. A set of upper teeth is associated with the upper jaw 101. The skull 10 also includes a mandible or lower jaw 100. A set of lower teeth is associated with lower jaw 100. Lower jaw 100 hinges at a joint 30 to skull 10. Joint 30 is called a temporomandibular joint (TMJ).

In one embodiment, a computer model of jaws 100 and 101 is generated. A computer simulation is capable of modeling interactions among the teeth on jaws 100 and 101. The computer simulation allows the system to focus on motions involving contacts between teeth mounted on the jaws. The computer simulation allows the system to render realistic jaw relationships which are physically correct when jaws 100 and 101 contact each other. The modeling of jaws 100 and 101 places the individual teeth in a treated position.

Further, the model can be used to simulate jaw movements including protrusive motions, lateral motions, and "tooth guided" motions where the path of lower jaw 100 is guided by teeth contacts rather than by anatomical limits of jaws 100 and 101. Motions are applied to one jaw, but may also be applied to both jaws. Based on the occlusion determination, the final arrangement of the teeth in jaws 100 and 101 can be ascertained.

As a result, an initial data set (IDDS) representing an initial tooth arrangement and a final digital data set (FDDS) representing a final tooth arrangement are generated. Based on both the IDDS and the FDDS, a plurality of intermediate digital data sets (INTDDSs) are defined to correspond to incrementally adjusted aligners. The INTDDSs are defined using techniques for aligning teeth (e.g., the standard arch method, etc.). Thereafter, a set of incremental position adjustment aligners are produced based on the INTDDs and the FDDS. The aligners are designed to be worn over the teeth and to reposition the teeth to each of the tooth arrangements.

Figure 2A:
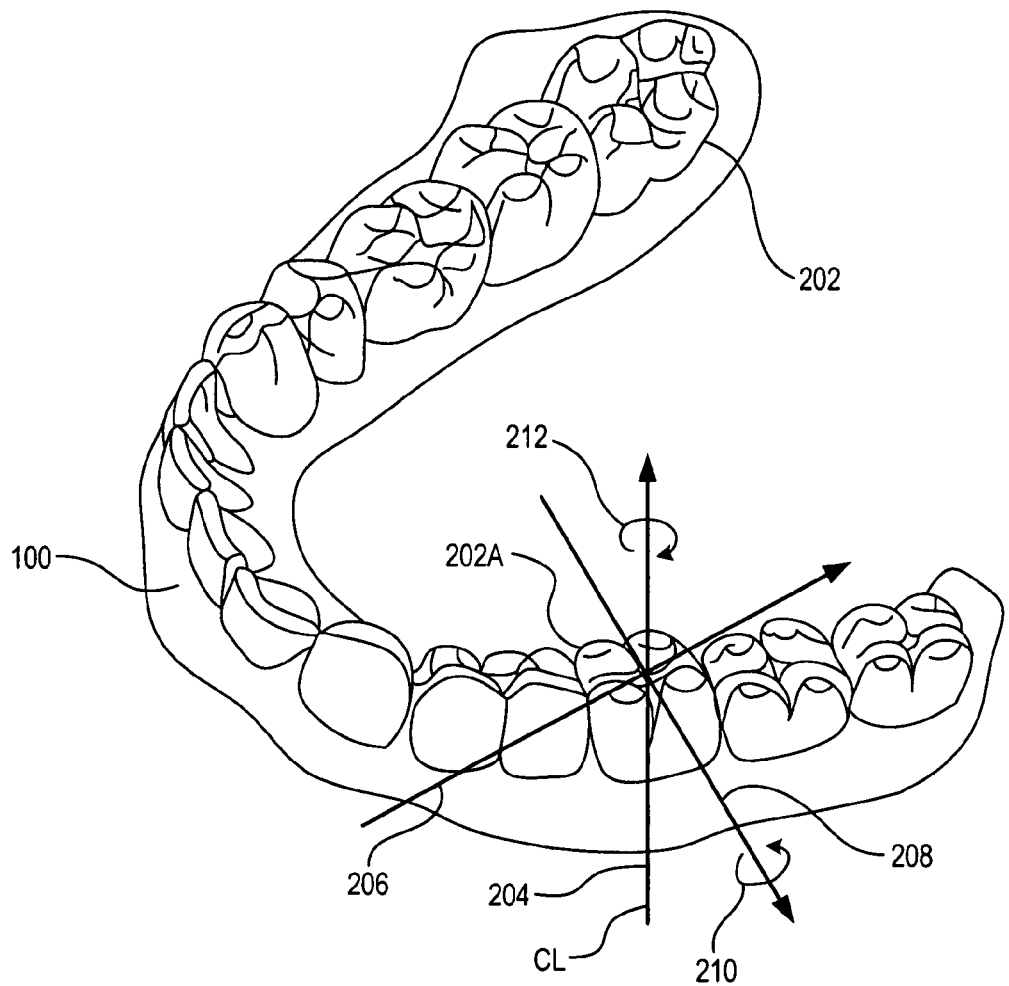
FIG. 2A illustrates in more detail the patient's lower jaw of FIG. 1 and provides a general indication of how a tooth may be moved by the method and apparatus of embodiments of the present invention.

Referring now to FIG. 2A, lower jaw 100 of FIG. 1 includes a plurality of teeth, typically shown as 202, for example, and is provided as an illustration of the repositioning of teeth through the use of an aligner, in accordance with one embodiment of the present invention. The lower jaw 100 of FIG. 2A typically includes up to sixteen teeth in the plurality of teeth 202, to include exemplary tooth 202A. Embodiments of the present invention are capable of moving at least one tooth of the plurality of teeth 202 from an initial tooth arrangement to a final tooth arrangement through a series of alignment stages.

In FIG. 2A, an arbitrary frame of reference is shown, and is used to describe how teeth in lower jaw 100 may be moved. For example, the frame of reference can be used to describe how tooth 202A is moved. An arbitrary centerline (CL) is drawn through exemplary tooth 202A. With reference to this centerline, the associated tooth may be moved in the orthogonal directions represented by axes 204, 206, and 208. As shown in FIG. 2A, axis 206 illustrates movement of tooth 202A between the anterior and posterior portions of lower jaw 100. Axis 210 illustrates side to side movement of tooth 202A in lower jaw 100. Axis 212 illustrates the upward and downward movements of tooth 202A in relation to lower jaw 100. In the configuration of FIG. 2A, the centerline corresponds to axis 204.

Additionally, the centerline may be rotated about the axis 208 (root angulation) and 204 (rotation) as indicated by arrows 210 and 212, respectively. Also, the exemplary tooth 202A may be rotated about the axis 206 (inclination). Thus, all possible free-form motions of tooth 202A can be performed.

A patient generally uses a repositioning aligner, corresponding to a given alignment stage in a treatment plan, until the aligner is no longer applying sufficient repositioning forces to the patient's teeth. When a patient first places an aligner over their teeth, the misalignment of the aligner with the teeth will apply forces on the teeth at the points of contact. Within the elastic range of the aligner material, the larger the misalignment, the stronger the repositioning force.

As the teeth gradually move into a desired arrangement for a given alignment stage and with the continued use of a corresponding aligner, the misalignment between the teeth and the aligner decreases and the applied force lessens. When the teeth substantially reach the desired configuration associated with the corresponding aligner, the force may approach zero. It is at this point that the useful life of such an aligner for applying repositioning force has ended. Once the dental biology has adapted to the new state, the patient may then progress to the next alignment stage in the treatment plan and begin wearing the next successive elastic repositioning aligner. The new aligner will apply repositioning forces to move the teeth to the next desired arrangement corresponding to the next alignment stage, repeating the aligner wear cycle.

In summary, the first aligner of a series of aligners will have a geometry selected to reposition a patient's teeth from the initial teeth arrangement to a first intermediate arrangement. After the first intermediate arrangement is approached or achieved, one or more additional, intermediate aligners will be successively placed on the teeth, where such additional aligners have geometries selected to progressively reposition teeth from the first intermediate arrangement through successive intermediate arrangement(s). The treatment will be finished by placing a final aligner in the patient's mouth, where the final aligner has a geometry selected to progressively reposition teeth from the last intermediate arrangement to the final tooth arrangement.

Figure 2B:
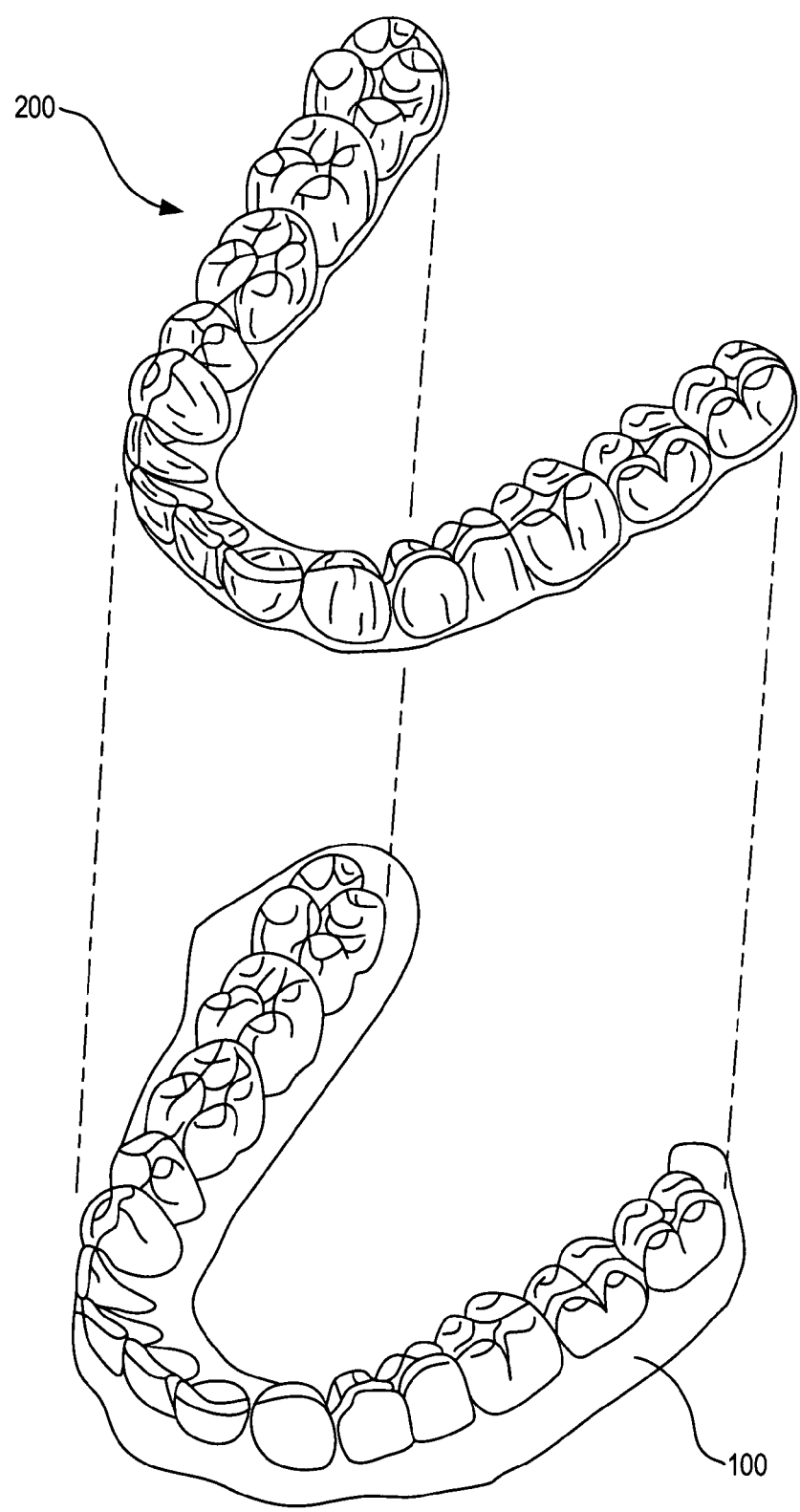
FIG. 2B illustrates the jaw of FIG. 1 together with an incremental polymeric shell dental appliance which has been configured according to the methods and apparatus of embodiments of the present invention.

Referring now to FIG. 2B, a single adjustment aligner 200 which is worn by the patient in order to achieve an incremental repositioning of individual teeth in lower jaw 100 of FIG. 1 is shown, in accordance with one embodiment of the present invention. The aligner 200 is one of a series of incremental position adjustment aligners worn by the patient to realign teeth from an initial arrangement to a final arrangement. For brevity and clarity, exemplary aligner 200 is shown for incremental repositioning of teeth in lower jaw 100; however, other embodiments are well suited to the use of aligners for repositioning of teeth in either or both the upper and lower jaws of a patient.

The exemplary aligner 200 comprises a polymeric shell having a cavity shaped to receive and resiliently reposition teeth from one tooth arrangement to a successive tooth arrangement. The polymeric shell will preferably, but not necessarily, fit over all teeth present in the upper or lower jaw (e.g., lower jaw 100). Often, only certain one(s) of the teeth will be repositioned while others of the teeth will provide a base or anchor region for holding the repositioning appliance in place as it applies the resilient repositioning force against the tooth or teeth to be repositioned.

In complex cases, however, many or most of the teeth will be repositioned at some point during the treatment. In such cases, the teeth which are moved can also serve as a base or anchor region for holding the repositioning appliance. Additionally, the gums and/or the palette can serve as an anchor region, thus allowing all or nearly all of the teeth to be repositioned simultaneously. Usually, no wires or other means will be provided for holding the aligner in place over the teeth. In some cases, however, it will be desirable or necessary to provide individual anchors on teeth with corresponding receptacles or apertures in the aligner 200 so that the aligner 200 can apply an upward force on the tooth which would not be possible in the absence of such an anchor.

The planning and fabrication of such aligners as an exemplary elastic polymeric positioning appliance is described in detail in U.S. Pat. No. 5,975,893, and in published PCT application WO 98/58596 which designates the United States and which is assigned to the assignee of the present application.

Systems of preformed aligners employing technology described in U.S. Pat. No. 5,975,893, are commercially available from Align Technology, Inc., Santa Clara, Calif., under the tradename, Invisalign System. Align Technology, Inc. is the assignee of the present application. The Invisalign System relies on designing and fabricating the aligners to be worn by the patient throughout treatment. The design of the aligners relies on computer modeling of a series of successive tooth arrangements, and the individual aligners are designed to be worn over the teeth and to reposition the teeth to each of the tooth arrangements. Usually, the set of aligners which is designed and fabricated at the outset of the treatment is able to successfully reposition the teeth to a final desired arrangement.

In embodiments of the present invention, multiple aligners of any given treatment may be planned and fabricated at the outset of treatment. As such, batches of aligners may thus be provided to the patient as a single package or system. The order in which the aligners are to be used will be clearly marked, (e.g. by sequential numbering) so that the patient can place the aligners over his or her teeth at a frequency prescribed by the orthodontist or other treating professional. Unlike braces, the patient need not visit the treating professional every time an adjustment in the treatment is made. While patients will usually want to visit their treating professionals periodically to assure that treatment is going according to the original plan, eliminating the need to visit the treating professional each time an adjustment is to be made allows the treatment to be carried out in many more, but smaller, successive steps while still reducing the time spent by the treating professional with the individual patient. Moreover, the ability to use polymeric shell appliances which are more comfortable, less visible, and removable by the patient, greatly improves patient compliance, comfort, and satisfaction.

Active Attachments for Applying Forces on Polymeric Shell Dental Appliances

Throughout the body of this Specification, the use of the terms "aligner" or "dental aligner" is synonymous with the use of the terms "appliance" and "dental appliance" in terms of dental applications. For purposes of clarity, embodiments of the present invention are hereinafter described within the context of the use and application of dental appliances, and more specifically "polymeric shell dental appliances," or "dental appliances."

Embodiments of the present invention are capable of eliciting tooth movement through the use of active attachment devices. The active attachment devices are capable of storing mechanical energy and releasing that energy over a period of time when in contact with a polymeric shell dental appliance. In addition, other embodiments are capable of redirecting the force in a different direction to enable additional tooth movements in such a way that overall orthodontic treatment is more effective. As a result, the activated attachment devices are capable of releasing its stored energy over a period of time in the form of prolonged and controlled tooth movement in a course of orthodontic treatment.

Figure 3A:
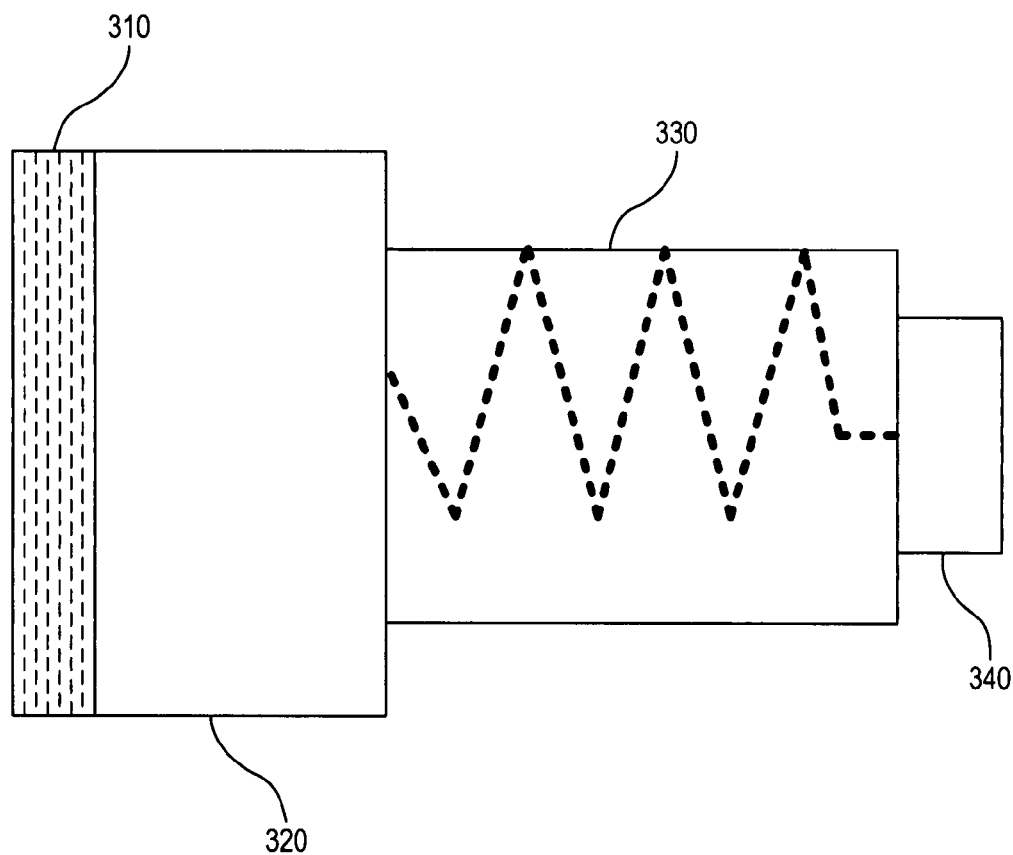
FIG. 3A is an illustration of an example active attachment device 300A that is capable of storing mechanical energy and releasing the mechanical energy over time to achieve orthodontic treatment, in accordance with one embodiment of the present invention.

FIG. 3A is an illustration of an example active attachment device 300A that is capable of storing mechanical energy and releasing the mechanical energy over time to achieve orthodontic treatment, in accordance with one embodiment of the present invention. Active attachment device 300A is bonded to a dental feature (e.g., surface of tooth) of a patient's dentition, whereby contact between active attachment device 300A and a polymeric shell dental appliance worn by the patient for orthodontic treatment activates active attachment device 300A. When activated, device 300A releases its stored mechanical energy over time in the form of controlled tooth movement.

As shown in FIG. 3A, active attachment device 300A comprises an anchoring attachment body 320. Anchoring attachment body 320 provides the base or structure upon which active attachment device 300 is built upon. As such, anchoring attachment body 320 is capable of being firmly bonded to a dental feature (e.g., surface of a tooth). That is, attachment body 320 acts as a substantially immovable base from which orthodontic forces can be applied.

The active attachment device 300A also comprises a bonding surface 310 that is coupled to anchoring attachment body 320. Bonding surface 310 is configured for anchoring the anchoring attachment body 320 to the dental feature. In one embodiment, a bonding feature is coupled to bonding surface 310. In one embodiment, the bonding feature comprises a bio-compatible adhesive. The bonding feature is configured to adhere bonding surface 310 to the dental feature. For example, bonding surface 310 is configured such that an adhesive can be placed on bonding surface 310 for purposes of fixedly attaching anchoring attachment body 320 to the dental feature, in one embodiment.

Active attachment device 300A also comprises a force-applying active mechanism 330 that is coupled to anchoring attachment body 320. In one embodiment, force-applying active mechanism 330 comprises a flexible structure extending from anchoring attachment body 320. Force-applying active mechanism 330 is capable of conferring flexibility to active attachment device 300A in order for energy to be stored. Further, the force-applying active mechanism 330 provides a force applying point between the dental feature and the polymeric shell dental appliance, when the polymeric shell dental appliance engages the force-applying active mechanism 330.

In the present embodiment, force-applying active mechanism 330 is shown as a spring-like structure for purposes of illustration only, and may take on any flexible shape or form. For example, embodiments of the force-applying active mechanism 330 comprise, but are not limited to the following flexible structures: wings, arms, loops, springs, slots, protrusion, extension, corrugated accordion design, rotational torque spring, etc. More specifically, force-applying active mechanism 330 is capable of storing or absorbing mechanical energy, when activated through bending, compression, or distortion of force-applying active mechanism 330. For example, when force-applying active mechanism 330 is deformed, mechanical energy is stored. The activated force-applying mechanism releases its stored mechanical energy by returning to its original extension. The activation and release of energy may be further enhanced with control of temperature change, ion change, light energy change, and/or chemical change in the environment.

In one embodiment a polymeric shell dental appliance is used to deform or compress and activate force-applying mechanism 330. For instance, the mechanical energy is stored as the polymeric shell dental appliance is snapped over the tooth that is coupled to active attachment device 300A. The mechanical energy stored in active attachment device 300A is controllably released in the form of controlled tooth movement. This effectively prolongs the useful life of the polymeric shell dental appliance. For instance, the polymeric shell dental appliance is able to work effectively over a greater period of time when using active attachment device 300A. Potentially, the use of active attachment device 300A may reduce the number of aligners needed per total orthodontic treatment.

As shown in FIG. 3A, active attachment device 300A comprises a polymeric shell dental appliance contact region 340 that is coupled to force-applying active mechanism 330. The polymeric shell dental appliance contact region 340 is configured to contact the polymeric shell dental appliance, in one embodiment. As such, force-applying active mechanism 340 is able to apply a force (e.g., distortion force) generated by force-applying active mechanism 330 between the dental feature and the polymeric shell dental appliance when the polymeric shell dental appliance engages the force-applying active mechanism 330. In embodiments of the present invention, the forces generated act to provide all movements of the corresponding tooth which includes, but is not limited to, the following movements: translation, inclination, intrusion, extrusion, rotation, angulation, etc.

Figure 3B:
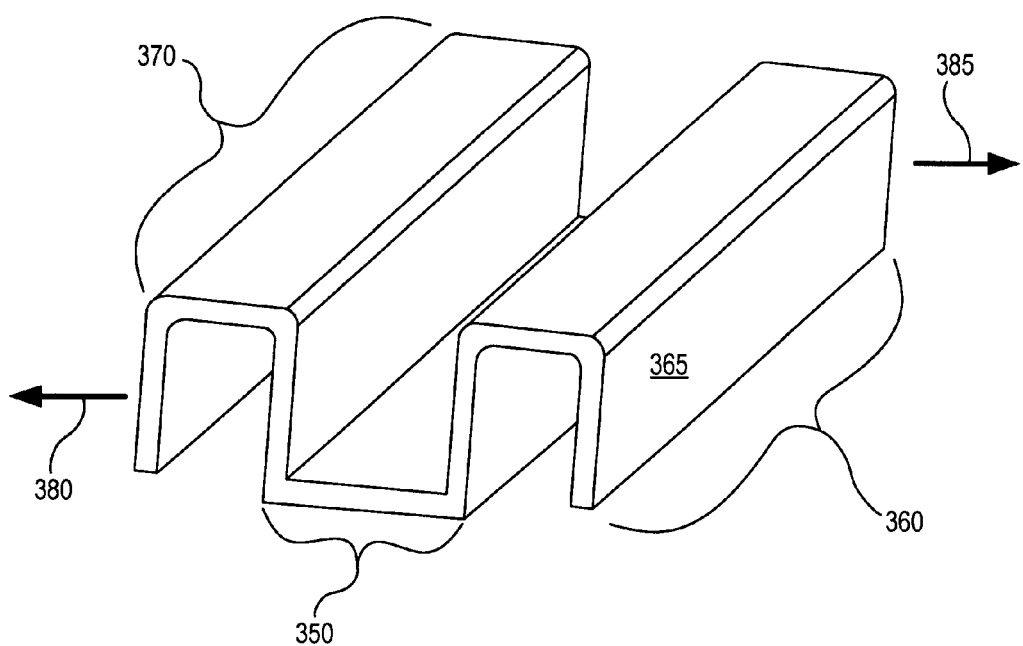
FIG. 3B is an illustration of an active attachment device that is capable of storing mechanical energy and releasing the mechanical energy over time to achieve orthodontic treatment, in accordance with one embodiment of the present invention.

FIG. 3B is a diagram illustrating an example active attachment device 300B, in accordance with one embodiment of the present invention. In one embodiment, the active attachment device 300B provides more details to the active attachment device 300A of FIG. 3A. The present embodiment illustrates an N-U-N structure, such as a corrugated structure, for active attachment device 300B. The active attachment device 300B comprises an elastic material (e.g., metal, plastic, etc.) with a shape that can be compressed for storing mechanical energy. In one embodiment, the active attachment device 300B comprises a thin metal sheet that is bent into an N-U-N structure.

In particular, the active attachment device 300B comprises an anchoring attachment body 350. The anchoring attachment body 350 is configured to provide a substantially rigid base from which forces are applied. As shown in FIG. 3B, the anchoring attachment body 350 comprises all or portions of the middle slot, U, structure of the active attachment device 300B.

The active attachment device 300B also comprises a bonding surface (not shown) coupled to anchoring attachment body 350. For example, the bonding surface is the underlying surface below the anchoring attachment body 350, in one embodiment. The bonding surface is configured for anchoring attachment body 350 to a dental feature of a patient's dentition. That is, the bonding surface allows for bonding the anchoring attachment body 350 to the surface of the tooth by a dental adhesive.

As shown in FIG. 3B, the active attachment device 300B comprises two force-applying mechanisms 360 and 370. The force-applying mechanism 360 and 370 are coupled to anchoring attachment body 350. As shown in FIG. 3B, each of the force-applying mechanisms 360 and 370 comprise all or part of the corresponding wing-like N structures of active attachment device 300B. Each of the force-applying mechanisms 360 and 370 is flexible and easy to compress or bend, and are capable of storing or absorbing mechanical energy when activated. Activation occurs when the corresponding force-applying mechanism 360 or 370 is bent, compressed, deformed, distorted, etc. from its original shape, in accordance with embodiments of the present invention. Release of energy is achieved when the corresponding force-applying mechanism 360 or 370 returns to its original shape.

For instance, force-applying mechanism 360, when distorted towards the base 350, applies a force in the direction shown by direction arrow 385. On the other hand, force-applying mechanism 370, when distorted towards the base 350, applies a force in the direction shown by direction arrow 380. As shown, the configuration of the active attachment device 300B provides for forces generated by the force-applying mechanisms 360 and 370 to be in opposite directions, in one embodiment. In other embodiments, the active attachment device is configured to generate forces by two or more force-applying mechanisms that are applied in generally the same or different directions. One or more the force-applying mechanisms can be activated to generate forces, such as, translational forces, rotational forces, distortional forces, etc.

In addition, each of the force-applying mechanisms 360 and 370 comprise a polymeric shell dental appliance contact region that is coupled to their corresponding force-applying active mechanism 360 or 370. For example, the polymeric shell dental appliance contact region 365 is coupled to the force-applying active mechanism 360. More particularly, each of the polymeric shell dental appliance contact regions 360 and 370 is configured to contact a polymeric shell dental appliance and apply a force generated by the corresponding force-applying active mechanism 360 or 370. The force generated is applied between the corresponding dental feature and the polymeric shell dental appliance when the polymeric shell dental appliance engages the force-applying active mechanism.

In one embodiment, active attachment device 300B is configured such that one or more polymeric shell dental appliances are used to activate force applying active mechanism 360 or 370. That is, in general, active attachment device 300B is capable of reuse, such that a force generated by active attachment device 300B is applied more than once between one or more polymeric shell dental appliances and the tooth upon which active attachment device 300B is attached.

FIGS. 4A-F illustrate the interactions of an active attachment device and a polymeric shell dental appliance, in accordance with embodiments of the present invention. Specifically, FIGS. 4A-F illustrate the movement of a tooth through the use of forces generated by the active attachment device of FIG. 3A in the course of orthodontic treatment, in accordance with embodiments of the present invention.

Figure 4A:
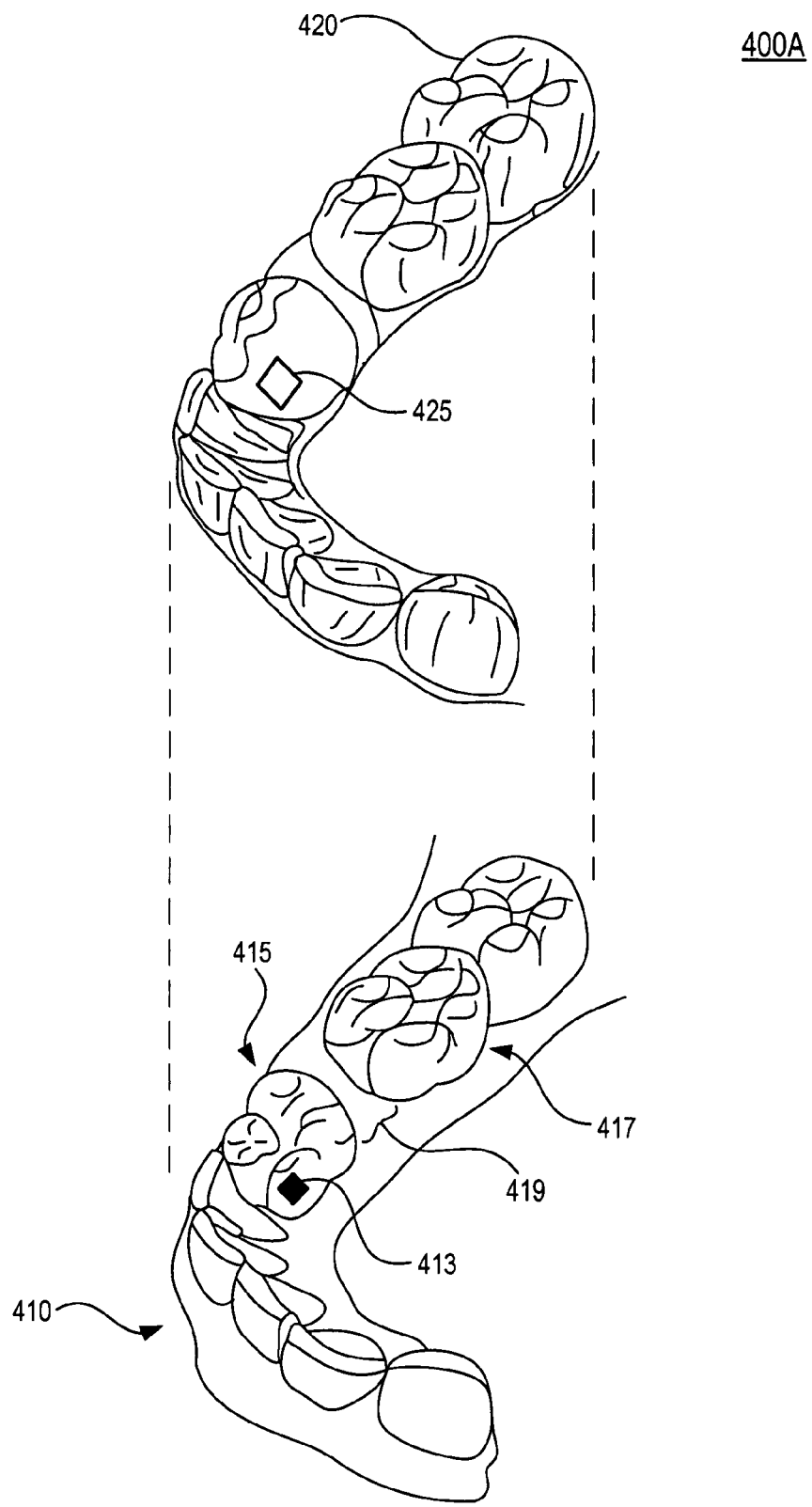
FIG. 4A shows a lower jaw together with a polymeric shell dental appliance illustrating the placement of an active attachment device and a corresponding contact region on a surface of a polymeric shell dental appliance, in accordance with one embodiment of the present invention.

Specifically, FIG. 4A shows a lower jaw 410 together with a polymeric shell dental appliance 420 illustrating the interaction of an active attachment device 413 and a polymeric shell dental appliance 420 for the purposes of moving a tooth 415 in the course of orthodontic treatment, in accordance with one embodiment of the present invention. Polymeric shell dental appliance 420 is shaped to receive and resiliently reposition a patient's dentition, including the tooth 415. For example, the active attachment device may be used to shorten the gap 419 between tooth 413 and tooth 417, in one embodiment.

In particular, FIG. 4A illustrates the placement of the active attachment device 413 on the tooth 415. The active attachment device 413 is shown generally as a darkened box in FIG. 4A. Further, the active attachment device 413 is configured to apply a force between the tooth and the polymeric shell dental appliance 420 when the polymeric shell dental appliance 420 engages a force-applying active mechanism in the active attachment device 413.

In addition, FIG. 4A illustrates a corresponding contact region 425 coupled to the polymeric shell dental appliance 425. The contact region 425 is shown generally as a box in FIG. 4A. Further, contact region 425 is configured to enable contact with the force-applying active mechanism of the active attachment device 413 that is fixedly attached to a dental feature of the tooth 415. Contact is achieved when the polymeric shell dental appliance is worn over the patient's dentition that includes tooth 415. In particular, the force-applying active mechanism applies a force between the dental feature of the tooth 415 and the polymeric shell dental appliance 420 at the contact region 425 when the polymeric shell dental appliance engages the force-applying active mechanism.

As a result, the interaction between the active attachment device 413 and the contact region 425 of the polymeric shell dental appliance 420 generates a combined force that can be oriented in any direction depending on the configuration of the contact region 425 and the active attachment device 413. That is, the generated force can be a translational force moving tooth 415 in a direction towards the posterior of the mouth, a direction towards the anterior of the mouth, a lingual direction towards the tongue, a facial direction towards the side of the mouth, a direction extending the tooth, a direction intruding the tooth, etc., or any combination of these directions, in embodiments of the present invention. The forces from the active attachments may also be used to counteract side-effect movements that can be inherent to certain types of tooth movements planned when using only the aligner alone as an orthodontic force generating device. For example, adding counter-tipping force when translating a tooth using the active attachment may help keep a moving tooth upright, because a tipping side-effect is possible when using just the aligner alone.

Figure 4B:
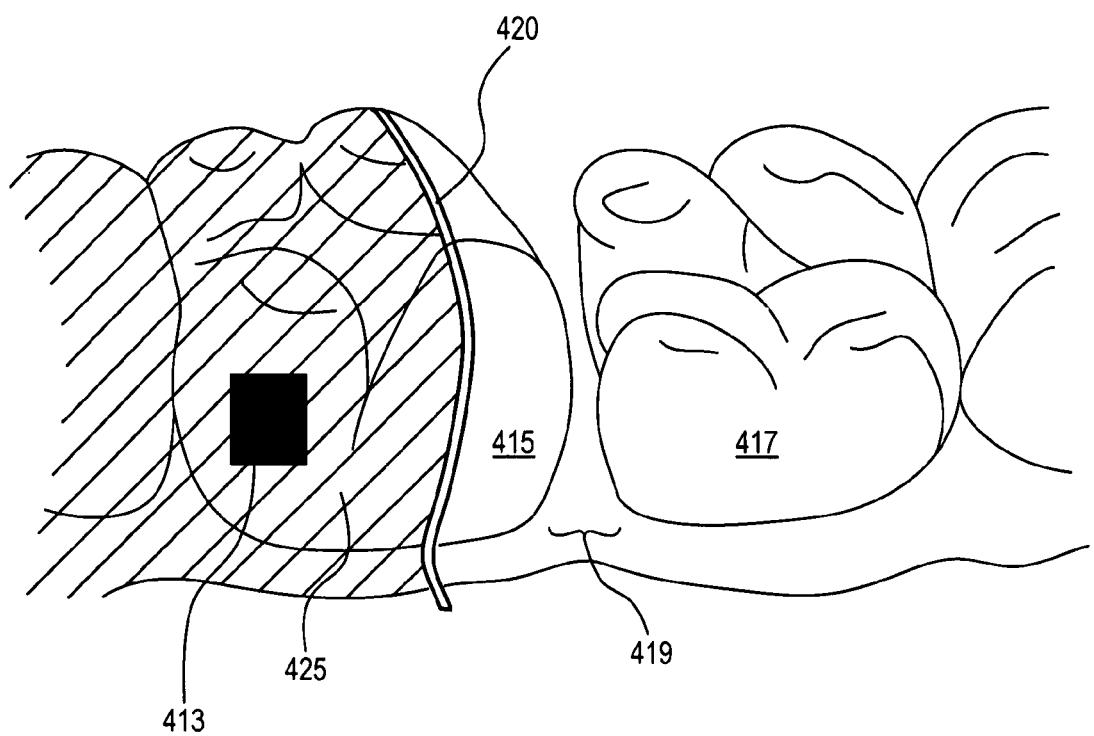
FIG. 4B illustrates the interaction of the active attachment device and the polymeric shell dental appliance, in accordance with one embodiment of the present invention.

FIG. 4B illustrates the interaction of the active attachment device 413 and the contact region 425 of the polymeric shell dental appliance 420, in accordance with one embodiment of the present invention. As shown in FIG. 4B, a partial representation of the polymeric shell dental appliance 420 is shown being worn over the patient's dentition. In particular, the polymeric shell dental appliance 420 is shown being worn over the tooth 420. As an advantage, active attachment device 413 of the present embodiment does not incorporate the use of archwires as in conventional braces. As such, the active attachment device 413 of embodiments of the present invention do not impede the flossing and brushing of a patient's dentition, as do conventional braces.

In addition, the contact region 425 of the polymeric shell dental appliance is shown covering the active attachment device 413. That is, the polymeric shell dental appliance 420 is shown engaging the active attachment device 413. More particularly, the contact region 425 is configured to contact the active attachment device 413 so that a force generated by the force-applying mechanism of the active attachment device 413 is applied between the tooth 415 and the polymeric shell dental appliance 420. In this manner, the generated force is used to move the tooth 415. For example, the generated force can be used to move tooth 415 closer to tooth 417 to reduce the gap 419 in the course of orthodontic treatment.

Figure 4C:
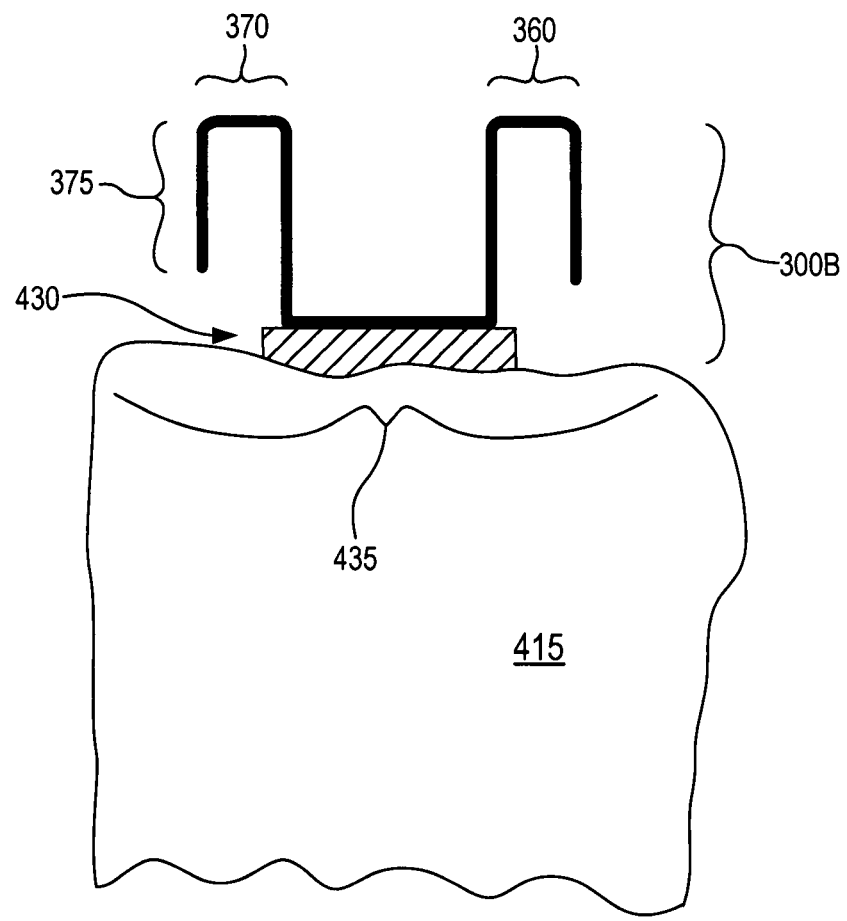
FIG. 4C is an illustration of the active attachment device of FIG. 3A bonded to a tooth in the orientation of FIGS. 4A and 4B, in accordance with one embodiment of the present invention.

FIG. 4C is a cross-sectional view of the tooth 415, in accordance with one embodiment of the present invention. In particular, FIG. 4C provides an illustration of the active attachment device 300B of FIG. 3B that is bonded to tooth 415 as described in FIGS. 4A and 4B, in accordance with one embodiment of the present invention. As shown, the active attachment device 300B is coupled to the side 435 of tooth 415. For instance, in one embodiment, the side 435 is the lingual side of tooth 415. Other embodiments are well suited to various placements of the active attachment device 300B, to include the facial side of tooth 415, occlusal side, etc.

In particular, as shown in FIG. 4C, the N structure, wing-like force applying mechanism 370 of the active attachment device 300B comprises a polymeric shell contact region 375. The polymeric shell contact region 375 is configured to contact polymeric shell dental appliance 420.

The active attachment device 300B is fixedly attached to the side 435 of the tooth 415 using a bonding feature 430, such as a bio-compatible adhesive, as previously described. The bonding feature 430 is configured to adhere the active attachment device 300B to the dental feature (e.g., side 435) of tooth 415, such that the active attachment device 300B is fixedly attached to the tooth 420.

Figure 4D:
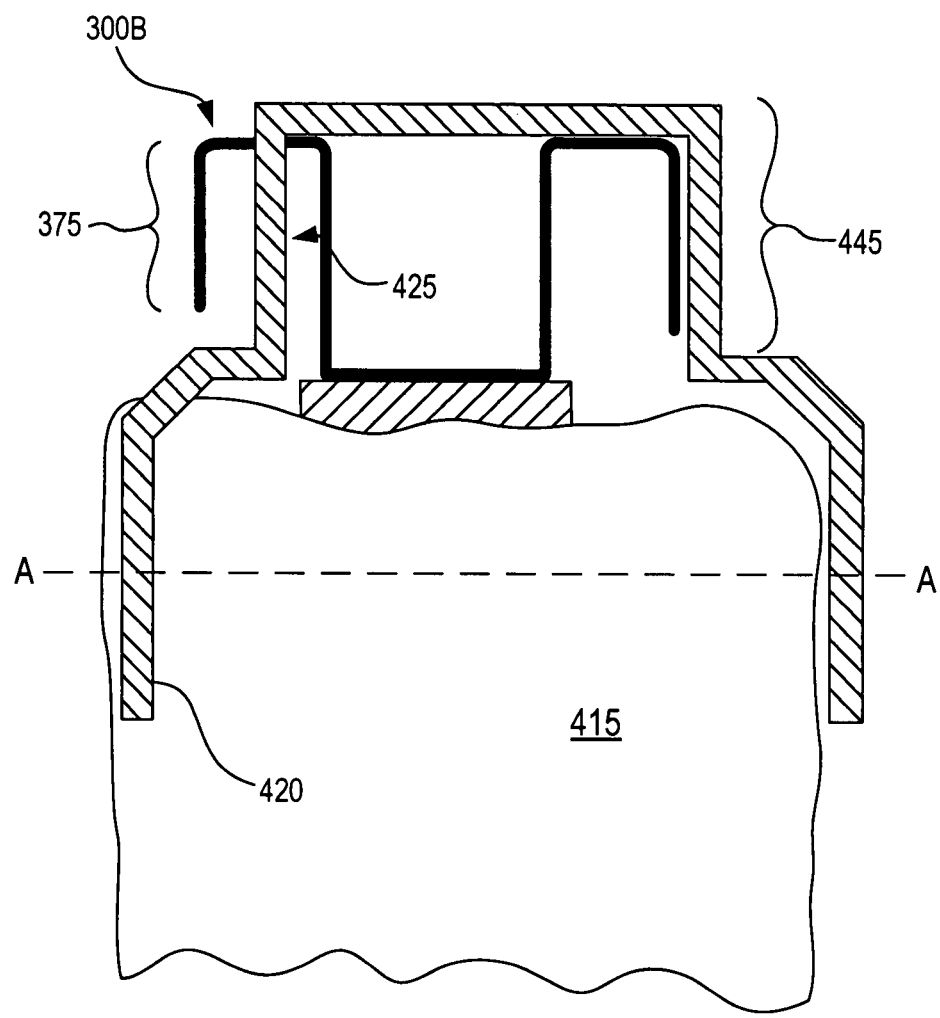
FIG. 4D is an illustration of the possible alignment between an active attachment device that is bonded to a tooth and a polymeric shell dental appliance, in accordance with one embodiment of the present invention.

FIG. 4D is a cross-sectional view of the tooth 415 along with the addition of an overlay of the polymeric shell dental appliance 420, in accordance with one embodiment of the present invention. As shown in FIG. 4D, the alignment of the polymeric shell dental appliance 420 and the active attachment device 300B is shown without any deformation of the active attachment device 300B to illustrate the relative positions and sizes of the polymeric shell dental appliance 420 in relation to the active attachment device 300B.

In particular, the active attachment device 300B comprises a receiving region 445 that is shown protruding away from the tooth 415. The receiving region 445 comprises a cavity in polymeric shell dental appliance 420 that is capable of enclosing portions or all of active attachment device 300B. More particularly, receiving region 445 is configured to accommodate wing-like, force-applying mechanisms 360 and 370 in force induced states and in relaxed states, in embodiments of the present invention, as will be described below in relation to FIGS. 4E and 4F.

Specifically, the width of the polymeric shell dental appliance 420 along line A-A is less than the width of tooth 415 along line A-A. As such, polymeric shell dental appliance 420 undergoes some deformation when the appliance 420 is worn over a patient's dentition. This deformation of the polymeric shell dental appliance 420 produces an orthodontic force that is used to move tooth 415. The orthodontic force of polymeric shell dental appliance 420 is applied by surface contact. This orthodontic force generated by the polymeric shell dental appliance 420 is reduced over time because of reduced elasticity. That is, the polymeric shell dental appliance 420 becomes permanently deformed after a period of time.

Additionally, the receiving region 445 of the polymeric shell dental appliance 420 is shown smaller than the active attachment device 300B, in their original configurations. As the active attachment device 300B is deformed to fit within the receiving region 445, mechanical energy is stored in the active attachment device 300B. For example, when the polymeric shell dental appliance is snapped into place, mechanical energy is stored in the active attachment device 300B. As such, as the size difference between the active attachment device 300B is increased, more mechanical energy can be stored in the active attachment device 300B.

Receiving region 445 comprises contact surface 425 of the polymeric shell dental appliance 420, as previously described. Contact surface 425 is configured to contact the force-applying mechanism of the active attachment device 300B, as will be shown in FIG. 4E. More specifically, the contact surface 425 is configured to contact the polymeric shell dental appliance contact region 375 that is coupled to the wing-like force-applying mechanism 370 of the active attachment device 300B.

In one embodiment, the receiving region 445 extends into a body of the polymeric shell dental appliance 420. That is, the receiving region 445 and the active attachment device 300B are small in comparison to the polymeric shell dental appliance. In another embodiment, the receiving region 445 extends beyond the body of the polymeric shell dental appliance 420, as shown in FIG. 4D.

In another embodiment, receiving region 445 is colored in such a way as to shield the active attachment device 300B from view. In particular, receiving region 445 is colored to shield from view the force-applying active mechanisms 360 and 370. In that manner, the unnoticeable characteristic of polymeric shell dental appliance 420 is maintained.

Figure 4E:
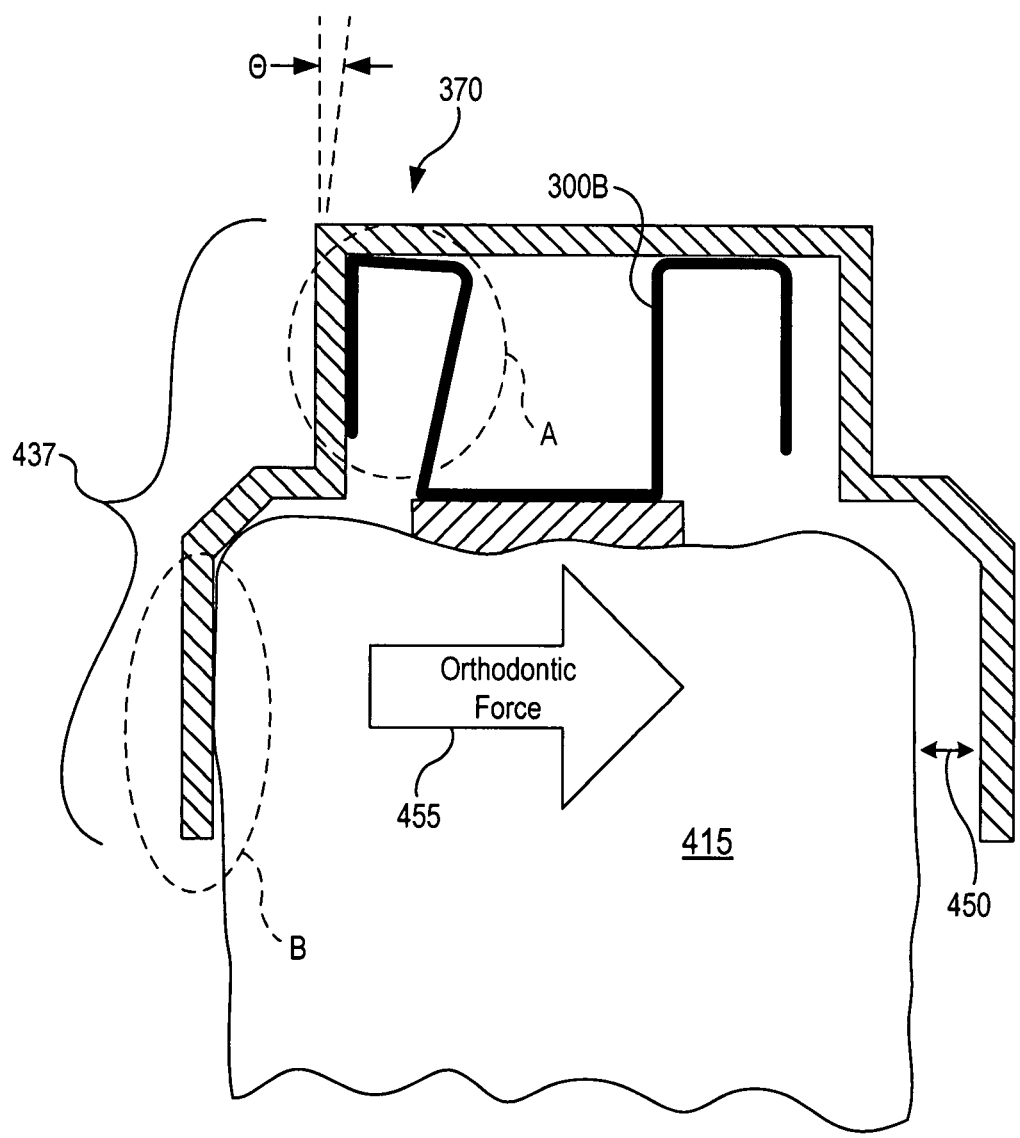
FIG. 4E is an illustration of the interaction between an activated active attachment device having stored mechanical energy and a polymeric shell dental appliance corresponding to a tooth in an initial position, in accordance with one embodiment of the present invention.

FIG. 4E is a cross-sectional view of the polymeric shell dental appliance 420 worn over the tooth 415, in accordance with one embodiment of the present invention. Tooth 415 is in an initial position that is displaced from a desired position. FIG. 4E illustrates the physical interaction between the polymeric shell dental appliance 420 and the active attachment device 300B given their alignment in FIG. 4D. As shown, the alignment of the polymeric shell dental appliance 420 and the active attachment device 300B produces a deformation of the active attachment device 300B when the polymeric shell dental appliance 420 is worn over tooth 415. That is, the polymeric shell dental appliance 420 is shown engaging the active attachment device 300B.

Two orthodontic forces act to move tooth 415. A first force is generated by polymeric shell dental appliance 420. A second force is generated by active attachment device 300B. Both of these forces combined are shown as orthodontic force 455.

As described previously, the first orthodontic force is generated by the deformation of polymeric shell dental appliance 420. Specifically, when worn over a patient's dentition, the deformation of polymeric shell dental appliance 420 is apparent by the angular deflection of the wall 437. Because tooth 415 is in an initial and displaced position when polymeric shell dental appliance 420 is first worn, a deformation occurs on the left side of polymeric shell dental appliance 420. For example, isolation area B illustrates the deformation of polymeric shell dental appliance 420 to fit around tooth 415. In particular, wall 437 of polymeric shell dental appliance 420 is deflected or deformed by an angle θ from its original position to fit over tooth 415.

In addition, a gap 450 is created due to the alignment of polymeric shell dental appliance 420, when worn, in relation to tooth 415. This first orthodontic force from polymeric shell dental appliance 420 acts to move tooth 415 such that gap 450 is gradually reduced as the tooth moves into its new pre-programmed position.

The second orthodontic force is generated by the active attachment device 300B, in accordance with one embodiment. Specifically, wing 370, as a force applying active mechanism, comprises polymeric shell dental appliance contact region 375, previously shown in FIGS. 4C and 4D. Contact region 375 is in contact with the polymeric shell dental appliance 420, when polymeric shell dental appliance 420 engages wing 370, as is shown in isolation area A. As such, the second orthodontic force is generated by the deformation of wing 370. The second orthodontic force from the active attachment device 300B also acts to move tooth 415 such that gap 450 is gradually reduced, in one embodiment. The elastic property of wing 370 will keep applying the second orthodontic force between polymeric shell dental appliance 420 and the tooth 415 to provide uninterrupted, long lasting force to move tooth 415. In particular, wing 370 will continue to apply the second orthodontic force long after application of the first orthodontic force from polymeric shell dental appliance 420 has expired, in one embodiment.

Figure 4F:
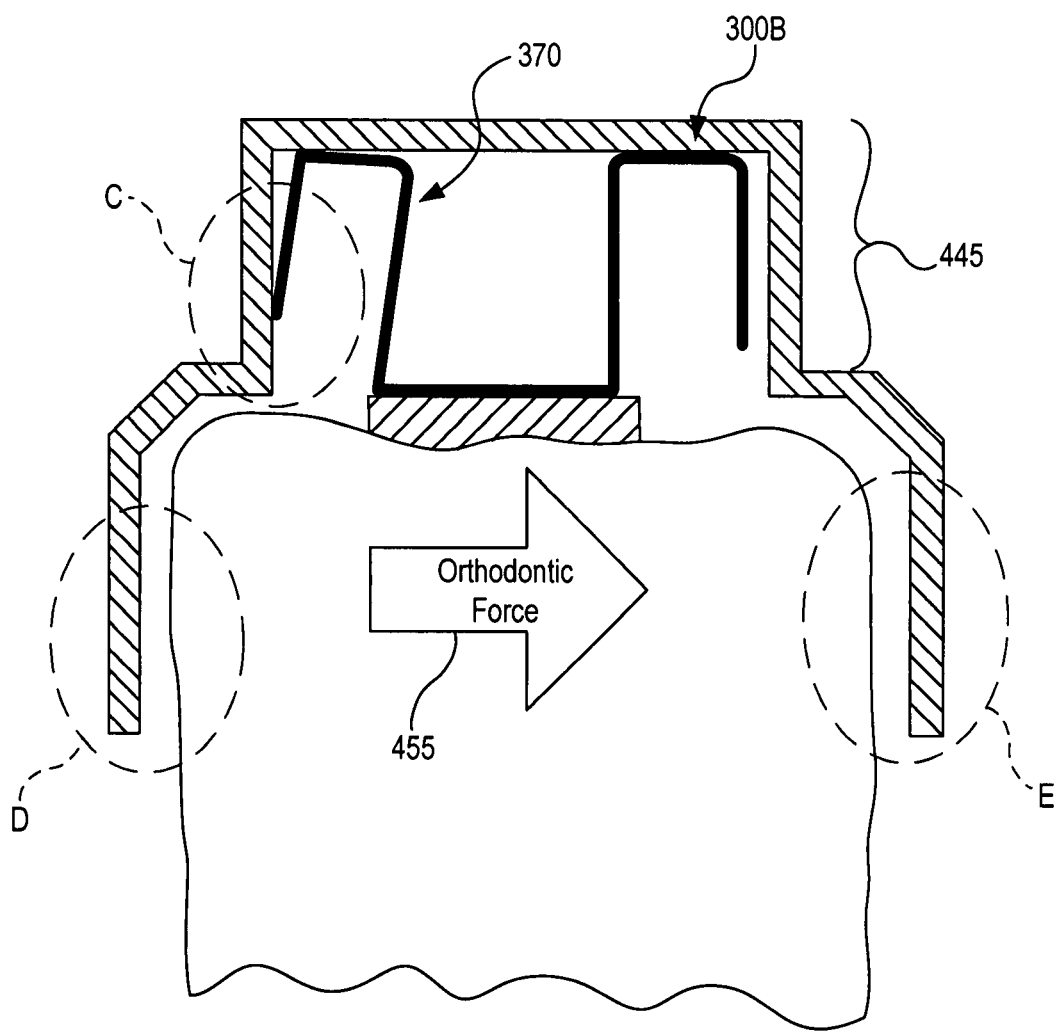
FIG. 4F is an illustration of the interaction between the active attachment device and polymeric shell dental appliance of FIG. 4B corresponding to a tooth in an intermediate position, in accordance with one embodiment of the present invention.

FIG. 4F is a cross-sectional view of polymeric shell dental appliance 420 worn over tooth 415, in accordance with one embodiment of the present invention. Tooth 415 is in an intermediate position after application of the combined orthodontic force 455. FIG. 4E illustrates the physical interaction between polymeric shell dental appliance 420 and the active attachment device 300B after the application of combined orthodontic force 455. In particular, tooth 415 has moved in such a way that gap 450 as shown in FIG. 4E is now substantially reduced.

The first orthodontic force from polymeric shell dental appliance 420 is substantially non-existent due in part to the substantially permanent deformation of polymeric shell dental appliance 420 due to its elastic properties (e.g., plastic properties), and the movement of tooth 415. As shown in FIG. 4E, isolation area D illustrates that there is no contact between polymeric shell dental appliance 420 and tooth 415. As such, the first orthodontic force from polymeric shell dental appliance 420 is no longer being applied. However, polymeric shell dental appliance 420 ensures that the tooth 415 does not move beyond the confines of the existing shell geometry, in order for the next appliance in the series to fit appropriately.

In addition, the second orthodontic force from polymeric shell dental appliance 420 is still being applied, but in a much reduced state. As shown in isolation area C, the receiving area 445 of polymeric shell dental appliance 420 is deformed and becoming larger due in part to the application of the second force as wing 370 returns to its relaxed state. However, as shown in FIG. 4E, wing 370 still is in contact with polymeric shell dental appliance 420 and will continue to generate the second orthodontic force as long as the cavity of receiving area 445 remains small enough such that wing 370 is deformed. The second orthodontic force will stop only after the cavity of receiving area 445 becomes big enough to hold all of active attachment 300B without any compression. Application of the second orthodontic force by the active attachment 300B lasts longer than the application of the first orthodontic force by polymeric shell dental appliance 420, in accordance with one embodiment of the present invention.

Figure 5:
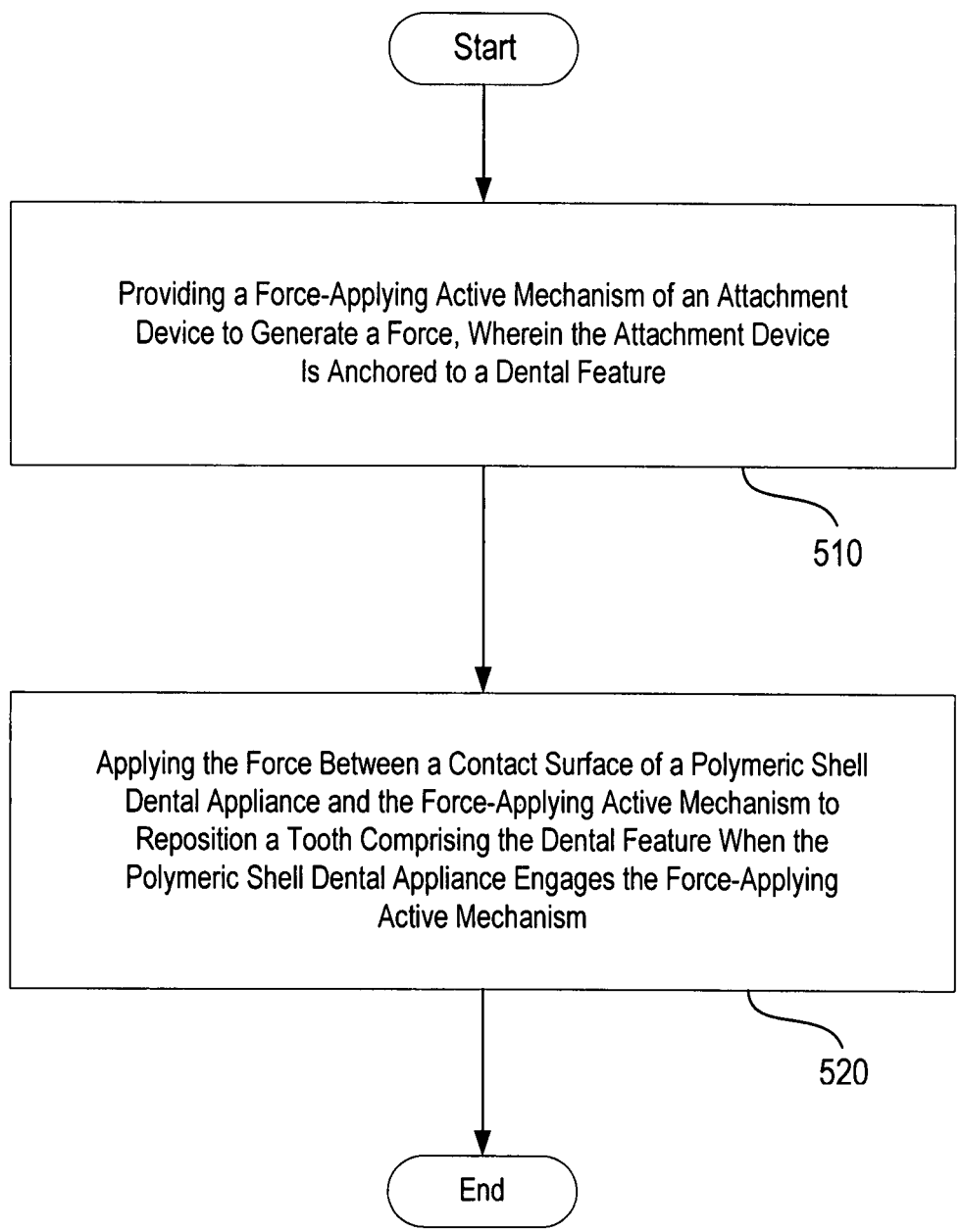
FIG. 5 is a flow chart of a method for enhancing forces generated by a polymeric shell dental appliance through the use of an active attachment device, in accordance with one embodiment of the present invention.

FIG. 5 is a flow chart of a method for enhancing forces generated by a polymeric shell dental appliance through the use of an active attachment device, in accordance with one embodiment of the present invention. The present embodiment provides an addition to the force applied by a polymeric shell dental appliance. As such, embodiments of the present invention are capable of providing uninterrupted, long lasting forces to moving one or more teeth.

At 510, the present embodiment provides a force-applying active mechanism of an attachment device to generate an orthodontic force. The attachment device is anchored to a dental feature of a patient's dentition. For example, the attachment device is anchored to a patient's tooth. More particularly, the force-applying active mechanism is capable of storing mechanical energy and releasing the energy over time. In one embodiment, the force-applying mechanism is deformed by placing at least one polymeric shell dental appliance over the patient's dentition.

For illustration, FIG. 4C shows an active attachment device 300B that is anchored to a tooth 415, wherein a force applying active mechanism 370 generates an orthodontic force. By varying the degree upon which the force applying active mechanism 370 is deformed, application of the orthodontic force can be controlled. That is, the greater the degree of deformation, the greater the orthodontic force that is applied. Conversely, less deformation leads to less orthodontic force that is applied.

In one embodiment, a bonding agent is applied to the attachment device to anchor the attachment device to the dental feature. In particular, a bonding agent is applied to a bonding surface of the attachment device, such that the attachment device is configured for anchoring to the dental feature by attaching the bonding surface to the dental feature.

At 520, the present embodiment applies the orthodontic force between contact surfaces of at least one polymeric shell dental appliance and the force-applying active mechanism. That is, for one polymeric shell dental appliance, contact is made between the polymeric shell dental appliance and the force-applying active mechanism at the contact surface. In particular, contact is made between the contact surface and a polymeric shell dental appliance contact region of the force-applying active mechanism. The polymeric shell contact region is configured to apply the orthodontic force between the dental feature and the polymeric shell dental appliance. As a result, the orthodontic force is used to reposition a tooth comprising the dental feature when the polymeric shell dental appliance engages the force-applying active mechanism.

In one embodiment, at least one force-applying mechanism is associated with at least one attachment device to generate a combined orthodontic force. For example, a first force-applying mechanism is coupled to a first attachment device to generate a first orthodontic force when a polymeric shell dental appliance is worn. Also, a second force-applying mechanism is coupled to a second attachment device to generate a second orthodontic force. The first and second attachment devices are coupled to a tooth of a patient's dentition, in one embodiment. The first and second orthodontic forces are combined to generate the combined orthodontic force that is applied to the tooth. For instance, the combined forces generate translational, rotational, distortional, etc. forces in embodiments of the present invention.

Figure 6:
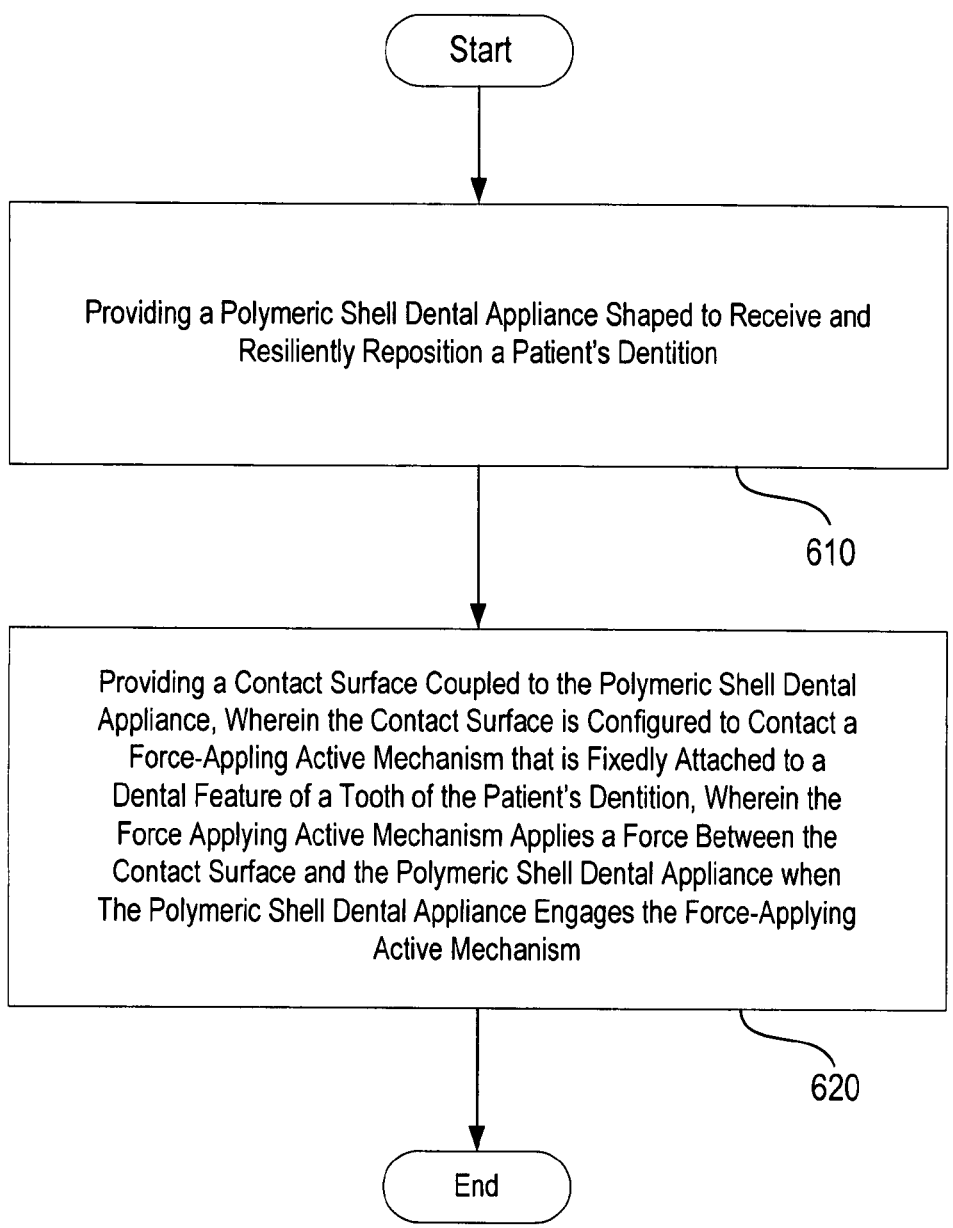
FIG. 6 is another flow chart of a method for enhancing forces generated by a polymeric shell dental appliance through the use of an active attachment device, in accordance with one embodiment of the present invention.

FIG. 6 is a flow chart of a method for enhancing forces generated for moving teeth, in accordance with one embodiment of the present invention. The present embodiment provides an addition to the force applied by a polymeric shell dental appliance. As such, embodiments of the present invention are capable of providing uninterrupted, long lasting forces to moving one or more teeth.

At 610, the present embodiment provides a polymeric shell dental appliance that is shaped to receive and resiliently reposition a patient's detention. In particular, the polymeric shell dental appliance is of a type that is removably placeable over the patient's dentition. That is, the polymeric shell dental appliance comprises a concave trough which conforms to at least one tooth when placed over the patient's dentition. The polymeric shell dental appliance is one of a series of incremental position adjustment appliances worn by the patient to realign teeth from an initial tooth arrangement to a final tooth arrangement. A full discussion of the use and application of the polymeric shell dental appliance is provided in relation to the discussion of aligner 200 of FIG. 2B.

At 620, the present embodiment provides a contact surface that is coupled to the polymeric shell dental appliance. The first contact surface is configured to contact a force-applying active mechanism that is fixedly attached to a dental feature of a tooth of the patient's dentition. As described previously with relation to FIG. 5, the force-applying active mechanism applies a force between the first contact surface and the polymeric shell dental appliance when the polymeric shell dental appliance engages the force-applying active mechanism.

The force-applying active mechanism is coupled to an anchoring attachment body. In particular, the present embodiment provides a bonding surface coupled to the anchoring attachment body, such that the bonding surface is configured to anchor the anchoring attachment body to the dental feature. In addition, a polymeric shell dental appliance contact region is coupled to the polymeric shell dental appliance in the present embodiment. The contact region is configured to contact a contact surface of the polymeric shell dental appliance to apply the force between the dental feature and the polymeric shell dental appliance when the polymeric shell dental appliance engages said first force-applying active mechanism.

In one embodiment, at least one contact surface is associated with the polymeric shell dental appliance used to generate a combined orthodontic force. For example, a first contact surface is configured to contact a first force applying active mechanism fixedly attached to a first dental feature of a tooth, in one embodiment. Also, a second contact surface is configured to contact a second force applying active mechanism fixedly attached to a second dental feature of the tooth. The first and second force-applying active mechanism generate a combined orthodontic force applied to the tooth. For instance, in one embodiment, the first and second contact surfaces are configured to generate a combined force that applies a translational force. In another embodiment, the first and second contact surfaces are configured to generate a combined force that applies a rotational force. In still another embodiment, the first and second contact surfaces are configured to generate a combined force that applies both translational and rotational forces.

Figure 7:
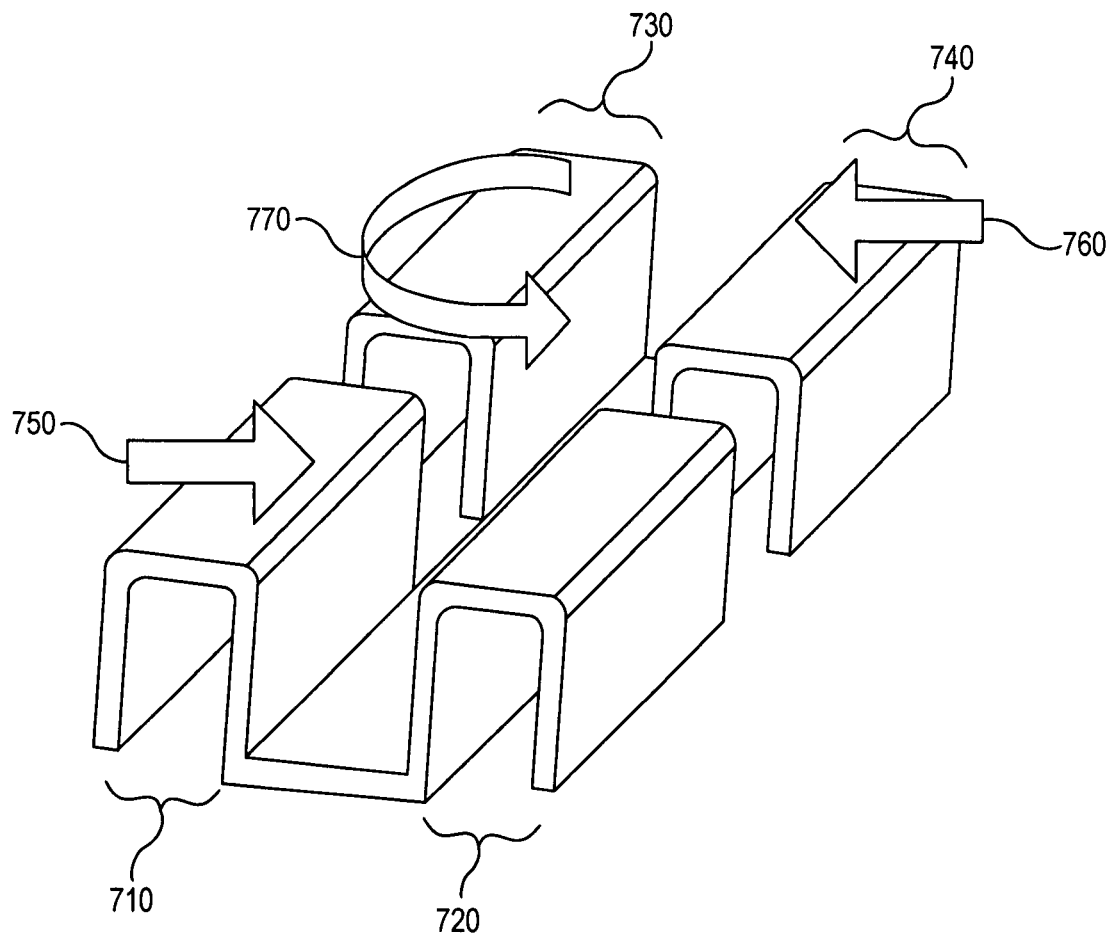
FIG. 7 is an illustration of an active attachment device capable of providing rotational forces, in accordance with one embodiment of the present invention.

FIG. 7 is an illustration of an active attachment device 700 capable of providing rotational moment forces, in accordance with one embodiment of the present invention. Previously, the active attachment device of FIG. 3A provides translational tooth movement in one dimension and at most two directions. As shown in FIG. 7, a combination of two such attachments will provide both transitional and rotation, in accordance with one embodiment of the present invention.

Active attachment device 700 comprises four wings, as follows: wing 710, wing 720, wing 730, and wing 740. As shown in FIG. 7, wings 710, 720, 730, and 740 combined form one active attachment device 700, in one embodiment. In other embodiments, wings 710, 720, 730, and 740 may comprise one or more N-U-N structures, as in the N-U-N structure of active attachment device 300B, in some embodiments. For instance, wings 710 and 720 may comprise a first N-U-N structure, and wings 730 and 740 may comprise a second N-U-N structure.

Forces are generated by compressing at least one of the wings 710, 720, 730, and 740. As shown orthodontic force 750 may be generated by compressing wing 710 taken alone or in combination with wing 730. By itself, orthodontic force 750 produces a translation force to move a tooth in one direction. Also, orthodontic force 760 may be generated by compressing wing 740 taken alone or in combination with wing 720. By itself, orthodontic force 760 produces a translation force to move a tooth in one direction. In one embodiment, if orthodontic force 750 is different from orthodontic force 760, then the combined forces generated is a rotational force 770. In one embodiment, the rotational force 770 produces a rotational movement of a tooth that is coupled to the active attachment device 700.

FIGS. 8A-D are diagrams of multi-directional active attachment devices, in accordance with embodiments of the present invention. The attachment devices of FIG. 8A-D comprise elastic materials (e.g., metal or plastic). In one embodiment, the attachment devices of FIG. 8A-D comprise plastic material. The plastic material is transparent or translucent, in one embodiment, such that the active attachment devices continue the low visibility characteristics of the polymeric shell dental appliance of embodiments of the present invention.

Figure 8A:
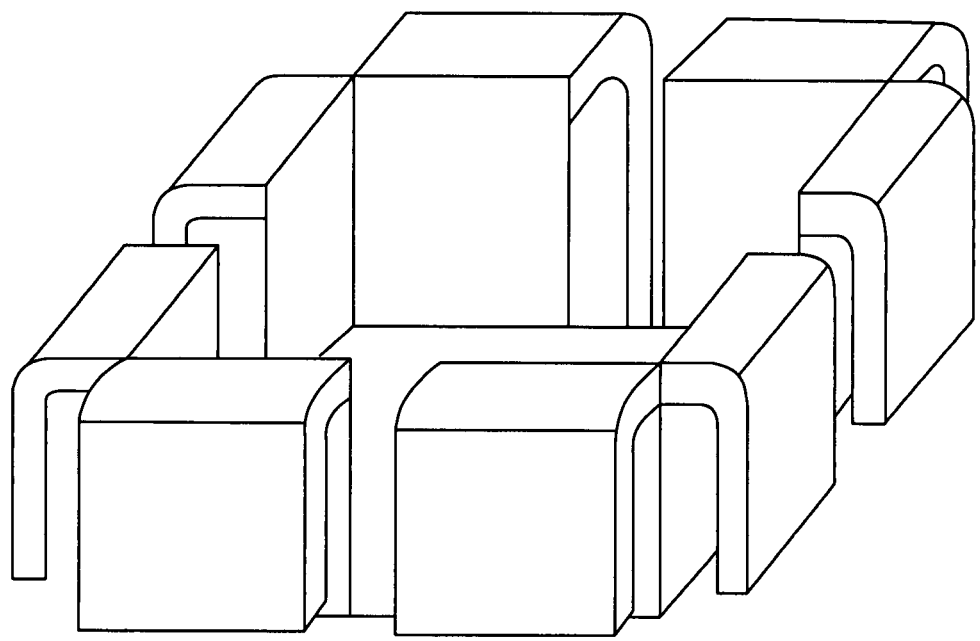
FIGS. 8A-D are diagrams of multi-directional active attachment devices, in accordance with embodiments of the present invention.

FIG. 8A illustrates an active attachment device 800A that comprises eight N-shaped edge blocks, in accordance with one embodiment of the present invention. Each of the N-shape edge blocks provides maximum flexibility for movement. Compression of one or more N-shape blocks provide for all forces (e.g., translational, rotational, distortional, etc.).

Figure 8B:
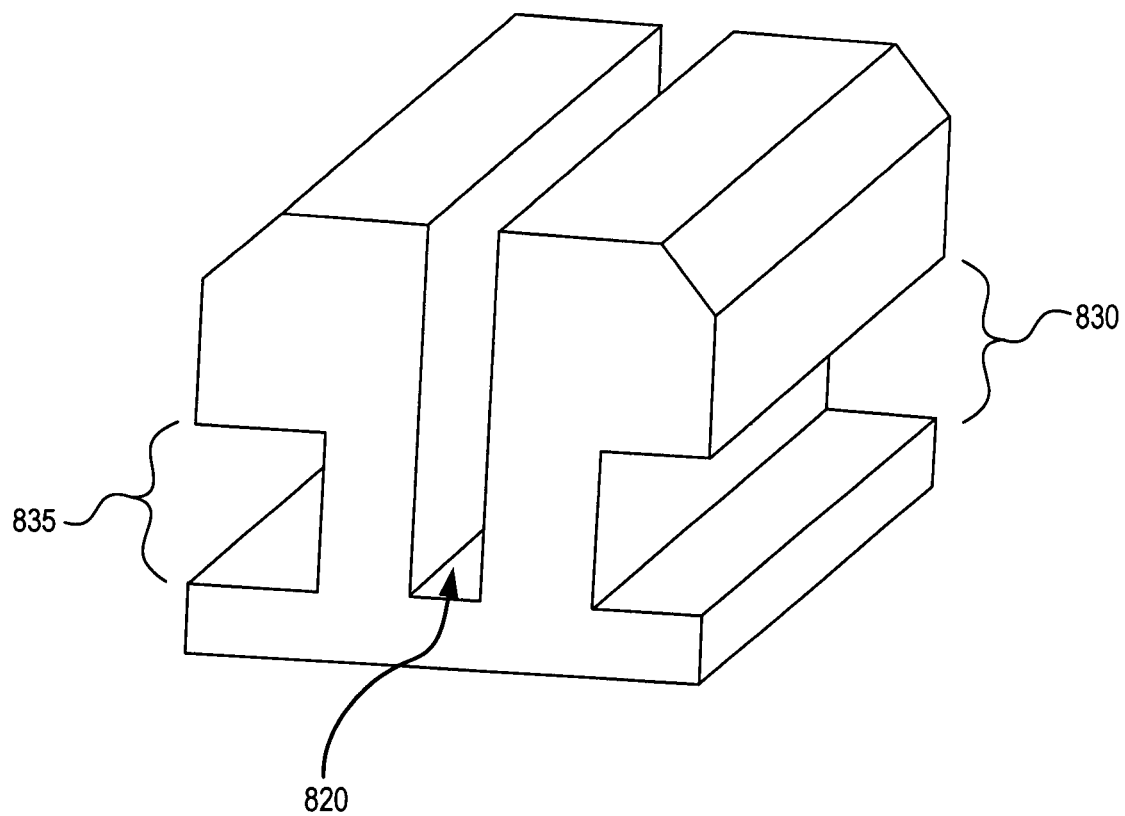

FIG. 8B illustrates a multi-directional active attachment device 800B, in accordance with one embodiment of the present invention. Active attachment device 800B comprises a block structure comprising a middle groove 820, and side grooves 830 and 835. The middle groove 820 and side grooves 830 and 835 provide room for the active attachment device 800B to bend and compress. As such, the active attachment device 800B provides one dimensional movement in two directions.

Figure 8C:
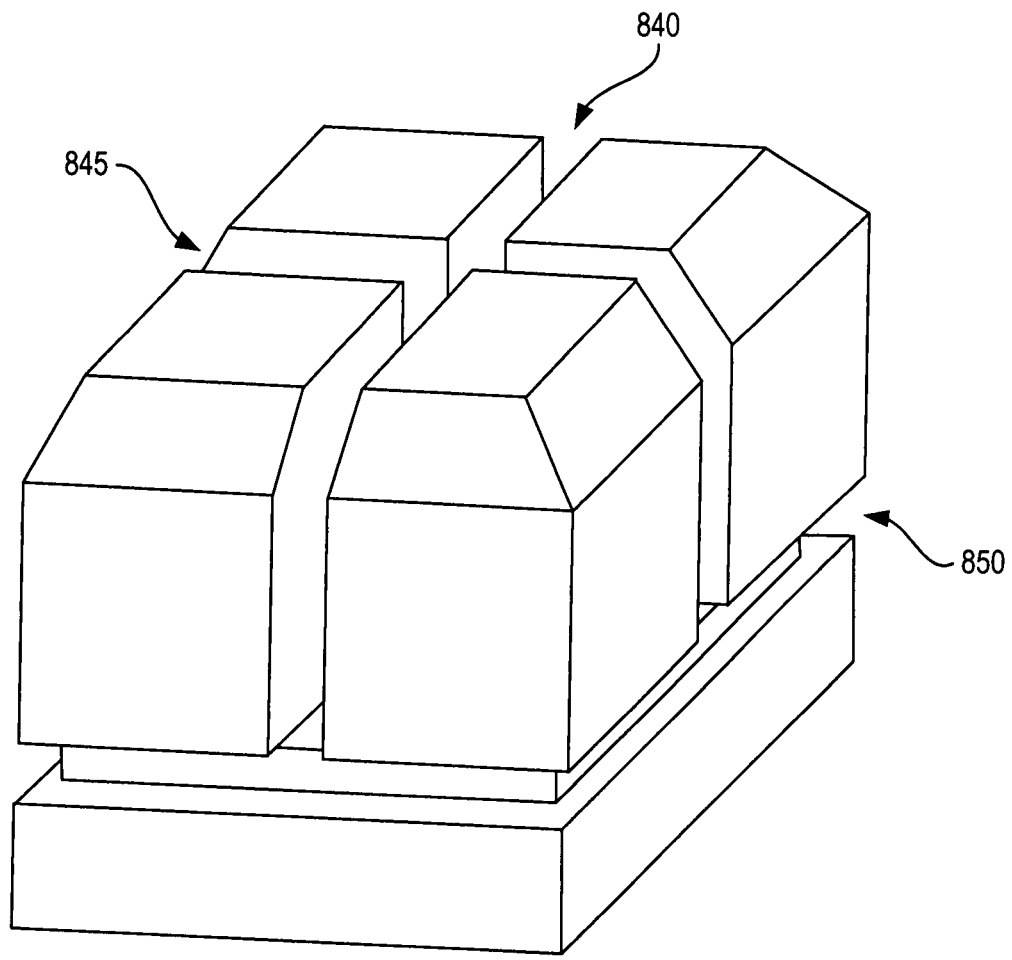

FIG. 8C illustrates a multi-directional active attachment device 800C, in accordance with one embodiment of the present invention. Active attachment device 800C is a combination of two or more attachment devices 800B, in embodiments of the present invention. That is, active attachment device 800C comprises a block structure comprising middle grooves 840 and 845, as well as a side groove 850 that is present on all sides of the active attachment device 800C. Active attachment device 800C provides 2-dimensional movement in four directions, and provides for rotational ability.

Figure 8D:
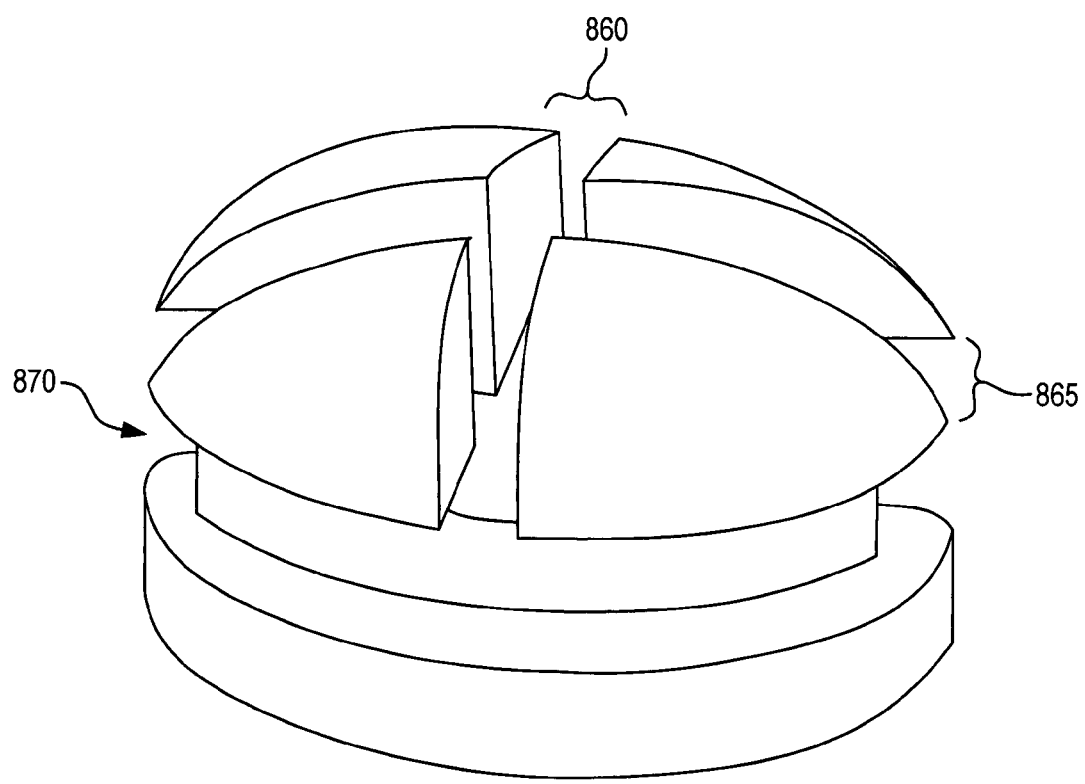

FIG. 8D illustrates a multi-directional active attachment device 800D, in accordance with one embodiment of the present invention. Active attachment device 800D illustrates the use of other shapes than blocks that can be deformed for purposes of generating orthodontic forces. As shown in FIG. 8D, active attachment device 800D comprises rounded surfaces to create smooth surfaces. That is, active attachment device 800D comprises a rounded structure comprising middle grooves 860 and 865, as well as a side groove 870 that circles active attachment device 800D. Active attachment device 800D provides 2-dimensional movement in four directions, and provides for rotational ability.

Various embodiments of the present invention disclose methods for enhancing resilient effects of dental appliances. For purposes of illustration, embodiments of the methods for enhancing resilient effects of dental appliances can be described as listed below.

A method for enhancing resilient effects of a dental appliance, comprising:

providing a force-applying active mechanism of an attachment device to generate a force, wherein said attachment device is configured to be anchored to a dental feature; and applying said force between said force-applying mechanism and a contact surface of a polymeric shell dental appliance when said polymeric shell dental appliance engages said force-applying active mechanism.

A method for enhancing resilient effects of a dental appliance, comprising: providing a polymeric shell dental appliance shaped to be worn over a patient's dentition;

providing a contact surface coupled to said polymeric shell dental appliance, wherein said contact surface is configured to contact a force-applying active mechanism that is fixedly attached to a dental feature, wherein said force-applying mechanism applies a force between said force-applying active mechanism and said contact surface.

More particularly, in one embodiment a method for enhancing effects of a dental appliance is disclosed. Specifically, the present embodiment provides a force-applying active mechanism of an attachment device. The force-applying active mechanism is capable of generating a force. In addition, the attachment device is configured to be anchored to a dental feature. Also, the present embodiment provides the force between the force-applying mechanism and a contact surface of a polymeric shell dental appliance. More particularly, the force is applied when the polymeric shell dental appliance engages the force-applying active mechanism.

In another embodiment, a method for enhancing effects of a dental appliance is disclosed. Specifically, the present embodiment provides a polymeric shell dental appliance. The dental appliance is configured to be worn over a patient's dentition. For example, the polymeric shell dental appliance comprises a concave trough that conforms to at least one tooth when placed over the patient's dentition. In addition, a contact surface is provided, wherein the contact surface is coupled to the polymeric shell dental appliance. That is, the contact surface is configured to contact a force-applying active mechanism that this fixedly attached to a dental feature of a patient's dentition. The force-applying active mechanism applies a force between the force-applying active mechanism and the contact surface. More particularly, the force-applying mechanism applies a force between the force-applying active mechanism and the contact surface when the polymeric shell engages the force-applying active mechanism.

Accordingly, various embodiments of the present invention disclose active attachment devices capable of interacting with polymeric shell dental appliances to apply forces used for orthodontic treatment. As a result, embodiments of the present invention provide for the above accomplishment, and further provide for the application of controlled forces over a large period of time when used with polymeric shell dental appliances. Still other embodiments of the present invention provide the above accomplishments, and further provide for a reduced number of polymeric shell dental appliances used in a course of orthodontic treatment. Other embodiments of the present invention provide the above accomplishments and further provide for complex movement of teeth previously unattainable through the sole use of polymeric shell dental appliances, which provides for more effective overall orthodontic treatment.

While the methods of embodiments illustrated in flow charts 500, and 600 show specific sequences and quantity of steps, the present invention is suitable to alternative embodiments. For example, not all the steps provided for in the method are required for the present invention. Furthermore, additional steps can be added to the steps presented in the present embodiment. Likewise, the sequences of steps can be modified depending upon the application.

Embodiments of the present invention, methods and system for applying thin films to polymeric shell dental appliances for improving dental esthetics have been described. While the invention is described in conjunction with the preferred embodiments, it is understood that they are not intended to limit the invention to these embodiments. On the contrary, the invention is intended to cover alternatives, modifications and equivalents, which may be included within the spirit and scope of the invention as defined by the appended claims. Furthermore, in the detailed description of the present invention, numerous specific details are set forth in order to provide a thorough understanding of the present invention. However, it will be recognized by one of ordinary skill in the art that the present invention may be practiced without these specific details. In other instances, well known methods, procedures, components, and circuits have not been described in detail as not to unnecessarily obscure aspects of the present invention.

What is claimed:

1. An attachment device for interacting with a polymeric shell dental appliance, said attachment device comprising:
an anchoring attachment body;
a bonding surface coupled to said anchoring attachment body, said bonding surface configured for anchoring said anchoring attachment body to a dental feature;
a force-applying active mechanism coupled to said anchoring attachment body; and
a polymeric shell dental appliance contact region coupled to said force-applying active mechanism, said polymeric shell dental appliance contact region configured to contact said polymeric shell dental appliance and apply a force generated by said force-applying active mechanism between said dental feature and said polymeric shell dental appliance when said polymeric shell dental appliance engages said force-applying active mechanism.

2. The attachment device of claim 1, further comprising:
a bonding feature coupled to said bonding surface, wherein said bonding feature is configured to adhere said bonding surface to said dental feature.

3. The attachment device of claim 2, wherein said bonding feature comprises a bio-compatible adhesive.

4. The attachment device of claim 1, wherein said force comprises a distortion force.

5. The attachment device of claim 1, wherein said force-applying active mechanism comprises a spring.

6. The attachment device of claim 1, wherein said force-applying active mechanism comprises a rotational torque spring.

7. The attachment device of claim 1, wherein said force-applying active mechanism comprises a wing structure.

8. The attachment device of claim 1, wherein said force-applying active mechanism comprises a corrugated structure.

9. An augmented system for repositioning teeth, said system comprising:
a polymeric shell dental appliance shaped to receive and resiliently reposition a patient's dentition; and
a first contact surface coupled to said polymeric shell dental appliance, wherein said first contact surface is configured to contact a first force-applying active mechanism that is fixedly attached to a first dental feature of a tooth of said patients dentition, wherein said first force-applying active mechanism applies a first force between said first dental feature and said polymeric shell dental appliance at said first contact surface when said polymeric shell dental appliance engages said first force-applying active mechanism.

10. The augmented system of claim 9, further comprising:
a first receiving region comprising said first contact surface, wherein said first receiving region extends into a body of said polymeric shell dental appliance.

11. The augmented system of claim 10, wherein said first receiving region is configured to accommodate said first force-applying mechanism in a force induced state and in a relaxed state.

12. The augmented system of claim 10, wherein said first receiving region is colored to shield said first force-applying active mechanism from view.

13. The augmented system of claim 9, wherein said first contact surface is located on an inner surface of said polymeric shell dental appliance, wherein said inner surface contacts a lingual surface of a tooth comprising said dental feature.

14. The augmented system of claim 9, wherein said first contact surface is located on an inner surface of said polymeric shell dental appliance, wherein said inner surface contacts a facial surface of a tooth comprising said dental feature.

15. The augmented system of claim 9, further comprising:
a second contact surface coupled to said polymeric shell dental appliance, wherein said second contact surface is configured to contact a second force-applying active mechanism that is fixedly attached to a second dental feature of said tooth, wherein said second force-applying active mechanism applies a second force between said second dental feature and said polymeric shell dental appliance at said second contact surface when said polymeric shell dental appliance engages said second force-applying active mechanism.

16. The augmented system of claim 15, wherein said first and second contact surfaces are configured such that said first and second forces combined apply a translational force.

17. The augmented system of claim 15, wherein said first and second contact surfaces are configured such that said first and second forces combined apply a rotational force.

18. A method for enhancing forces generated by a polymeric shell dental appliance, comprising:
providing a first force-applying active mechanism of a first attachment device to generate a first force, wherein said first attachment device is anchored to a first dental feature; and
applying said first force between a first contact surface of said polymeric shell dental appliance and said first force-applying active mechanism to reposition a tooth comprising said first dental feature when said polymeric shell dental appliance engages said first force-applying active mechanism.

19. The method of claim 18, wherein said anchoring a first attachment device comprises:
applying a bonding agent to a bonding surface of said first attachment device that is configured for anchoring said first attachment device to said first dental feature; and
attaching said bonding surface to said first dental feature.

20. The method of claim 18, wherein said providing said force-applying active mechanism comprises:
deforming said first force-applying active mechanism by placing said polymeric shell dental appliance over a patient's dentition comprising said tooth.

21. The method of claim 20, wherein said deforming said force-applying active mechanism further comprises:
varying a degree of deformation of said first force-applying active mechanism to control application of said first force.

22. The method of claim 18, wherein said applying said first force comprises:
providing contact between a polymeric shell dental appliance contact region and said first contact surface, wherein said first force-applying active mechanism comprises said polymeric shell contact region that is configured to apply said first force against said polymeric shell dental appliance.

23. The method of claim 18, further comprising:
providing a second force-applying active mechanism of a second attachment device to generate a second force, wherein said second attachment device is anchored to a second dental feature of said tooth; and
applying a rotational force to reposition said tooth by applying said second force against a second contact surface of said polymeric shell dental application to reposition said tooth.

24. The method of claim 18, further comprising:
applying said first force against a second contact surface of a second polymeric shell dental appliance to reposition said tooth.

25. A method for enhancing forces generated for moving teeth, said method comprising:
providing a polymeric shell dental appliance shaped to receive and resiliently reposition a patient's dentition;
providing a first contact surface coupled to said polymeric shell dental appliance, wherein said first contact surface is configured to contact a first force-applying active mechanism that is fixedly attached to a first dental feature of a tooth of said patients dentition, wherein said first force-applying active mechanism applies a first force between said first contact surface and said polymeric shell dental appliance when said polymeric shell dental appliance engages said first force-applying active mechanism.

26. The method of claim 25, further comprising:
providing an anchoring attachment body;
providing a bonding surface that is coupled to said anchoring attachment body, wherein said bonding surface is configured for anchoring said anchoring attachment body to a dental feature;
providing said first force-applying active mechanism that is coupled to said anchoring attachment body; and
providing a polymeric shell dental appliance contact region that is coupled to said first force-applying active mechanism, wherein said polymeric shell dental appliance contact region is configured to contact said first contact surface of said polymeric shell dental appliance and apply said first force against said polymeric shell dental appliance when said polymeric shell dental appliance engages said first force-applying active mechanism.

27. The method of claim 25, further comprising:
providing a second contact surface coupled to said polymeric shell dental appliance, wherein said second contact surface is configured to contact a second force-applying active mechanism that is fixedly attached to a second dental feature of said tooth, wherein said second force-applying active mechanism applies a second force between said second contact surface and said polymeric shell dental appliance when said polymeric shell dental appliance engages said second force-applying active mechanism.

28. The method of claim 27, further comprising:
configuring said first and second contact surfaces such that said first and second forces combined apply a translational force.

29. The method of claim 27, further comprising:
configuring said first and second contact surfaces such that said first and second forces combined apply a rotational force.

30. The method of claim 27, further comprising:
Configuring said first and second contact surfaces such that said first and second forces combined apply a translational and rotational force.

* * * * *